(12) United States Patent
Mattson

(10) Patent No.: US 8,119,629 B2
(45) Date of Patent: Feb. 21, 2012

(54) CARBOXAMIDE GABA$_A$ α2 MODULATORS

(75) Inventor: Ronald J. Mattson, Meriden, CT (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 589 days.

(21) Appl. No.: 12/240,237

(22) Filed: Sep. 29, 2008

(65) Prior Publication Data

US 2009/0093466 A1 Apr. 9, 2009

Related U.S. Application Data

(60) Provisional application No. 60/977,095, filed on Oct. 3, 2007.

(51) Int. Cl.
*A61K 31/55* (2006.01)
*C07D 487/12* (2006.01)

(52) U.S. Cl. ......................... 514/220; 540/562

(58) Field of Classification Search .................. 540/562; 514/220

See application file for complete search history.

(56) References Cited

U.S. PATENT DOCUMENTS

| | | | | |
|---|---|---|---|---|
| 4,280,957 | A | * | 7/1981 | Walser et al. ........... 540/562 |
| 4,401,597 | A | | 8/1983 | Walser et al. |
| 5,317,018 | A | * | 5/1994 | Walser et al. ........... 514/220 |
| 2004/0082573 | A1 | | 4/2004 | Cook et al. |

FOREIGN PATENT DOCUMENTS

| | | |
|---|---|---|
| EP | 0 109 921 | 5/1984 |
| EP | 0 135 770 | 4/1985 |
| EP | 0 573 982 | 12/1993 |
| WO | WO 99/63933 | 12/1999 |
| WO | WO 03/013545 | 2/2003 |
| WO | WO 03/029272 | 4/2003 |
| WO | WO 03/082832 | 10/2003 |
| WO | WO2006/004945 A1 | 1/2006 |

OTHER PUBLICATIONS

Liu et al. "Synthesis and pharmacological properties of Novel 8-substituted imidazobenzodiazepines: High-affinity, selective probes for alpha5-containing GABAa receptors," J. Med. Chem. 1996, vol. 39, pp. 1928-1934.*

He, X. et al., "Pharmacophore/Receptor Models for GABA$_A$/BzR α2β3γ2, α3β3γ2 and α4β3γ2 Recombinant Subtypes. Included Volume Analysis and Comparison to α1β3γ2, α5β3γ2 and α6β3γ2 Subtypes", Drug Design and Discovery, vol, 17, pp. 131-171 (2000).

Huang, Q. et al., "Pharmacophore/Receptor Models for GABA$_A$/BzR Subtypes (α1β3γ2, α5β3γ2 and α6β3γ2) via a Comprehensive Ligand-Mapping Approach", Journal of Medicinal Chemistry, vol. 43, No. 1, pp. 71-95 (2000).

M. M. Savic, "Are GABA$_A$ Receptors Containing Alpha5 Subunits Contributing to the Sedative Properties of Benzodiazepine Site Agonists?," Neuropsychopharmacology, 33(2), pp. 332-339, 2008.

D. Han, "A Study of the Structure-Activity Relationship of GABA$_A$-Benzodiazepine Receptor Bivalent Ligands by Conformational Analysis with Low Temperature NMR and X-Ray Analysis," Bioorganic & Medicinal Chemistry, 16(19), pp. 8853-8862, 2008.

* cited by examiner

*Primary Examiner* — Shengjun Wang
(74) *Attorney, Agent, or Firm* — James Epperson

(57) ABSTRACT

The invention encompasses compounds of Formula I, including pharmaceutically acceptable salts, their pharmaceutical compositions, and their use in treating CNS disorders.

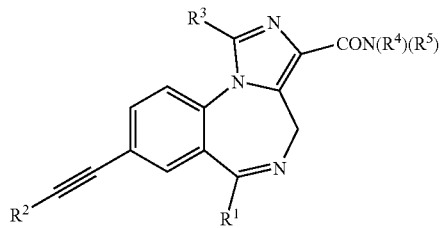

6 Claims, No Drawings

CARBOXAMIDE GABA$_A$ α2 MODULATORS

CROSS REFERENCE TO RELATED APPLICATIONS

This application claims the benefit of U.S. provisional application No. 60/977,095, filed Oct. 3, 2007.

BACKGROUND OF THE INVENTION

Benzodiazepines, high-efficacy, non-subtype selective GABA$_A$ positive modulators, are fast-onset anxiolytics with a number of side effects, such as sedation, motor incoordination, abuse liability, dependence, and memory impairment. Studies using point mutations introduced into the mouse genome (knock-in mutations) have suggested that GABA$_A$/α2 subunit-containing receptors mediate anxiolytic effects and GABA$_A$/α1 subunit-containing receptors mediate sedative/ataxic effects of classical benzodiazepines. In addition, GABA$_A$/α1-selective compounds, such as zolpidem (Ambien®), are clinically used as sedative/hypnotics. Compounds with high intrinsic efficacy at the GABA$_A$/α2 receptors and reduced intrinsic efficacy at the GABA$_A$/α1 receptors show reduced potential for motoric side effects and possibly reduced abuse liability, while retaining anxiolytic-like activity in preclinical models. Thus, a compound with functional selectivity for the GABA$_A$/α2 receptors has the potential to be a non-sedating anxiolytic.

DESCRIPTION OF THE INVENTION

One aspect of the invention are compounds of formula I

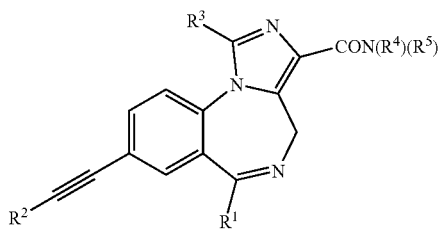

I $R^1$ is phenyl, thienyl, or pyridinyl, and is substituted with 0-2 substituents selected from halo, alkyl, cyano, and nitro;
$R^2$ is hydrogen, alkyl, or cycloalkyl;
$R^3$ is hydrogen, alkyl, cycloalkyl, haloalkyl, alkenyl, or alkynyl;
$R^4$ is hydrogen, alkyl, cycloalkyl, (cycloalkyl)alkyl, hydroxyalkyl, alkoxyalkyl, (alkoxy)$_2$alkyl, (cycloalkyl)alkoxyalkyl, (alkylCO$_2$)alkyl, (CO$_2$R$^6$)alkyl, (COR$^7$)alkyl, (R$^9$)alkyl, (tetrahydrofuranyl)alkyl, or (furanyl)alkyl;
$R^5$ is hydrogen, alkyl, cycloalkyl, (cycloalkyl)alkyl, hydroxyalkyl, alkoxyalkyl, (alkoxy)$_2$alkyl, (cycloalkyl)alkoxyalkyl, (alkylCO$_2$)alkyl, (CO$_2$R$^6$)alkyl, (COR$^7$)alkyl, (R$^9$)alkyl, (tetrahydrofuranyl)alkyl, or (furanyl)alkyl;
or N(R$^4$)(R$^5$) taken together is azetidinyl, pyrrolidinyl, piperidinyl, piperazinyl, morpholinyl, homopiperidinyl, homopiperazinyl, or homomorpholinyl, and is substituted with 0-3 substituents selected from oxo, alkoxy, hydroxyl, alkyl, pyridinyl, and pyrimidinyl;
$R^6$ is hydrogen, or alkyl;
$R^7$ is hydrogen, or alkyl;
$R^8$ is hydrogen, alkyl, or cycloalkyl; and
$R^9$ is amino, alkylamino, dialkylamino, azetidinyl, pyrrolidinyl, piperidinyl, piperazinyl, morpholinyl, homopiperidinyl, homopiperazinyl, or homomorpholinyl;
or a pharmaceutically acceptable salt thereof.

Another aspect of the invention is a compound of formula I where:
$R^1$ is phenyl, thienyl, or pyridinyl, and is substituted with 0-2 substituents selected from halo, alkyl, cyano, and nitro;
$R^2$ is hydrogen, alkyl, or cycloalkyl;
$R^3$ is hydrogen, alkyl, cycloalkyl, haloalkyl, alkenyl, or alkynyl;
$R^4$ is hydrogen, alkyl, cycloalkyl, hydroxyalkyl, alkoxyalkyl, (CO$_2$R$^6$)alkyl, or (COR$^7$)alkyl;
$R^5$ is hydrogen, alkyl, cycloalkyl, hydroxyalkyl, alkoxyalkyl, (R$^6$R$^7$N)alkyl, (CO$_2$R$^8$)alkyl, or (COR$^9$)alkyl;
or N(R$^4$)(R$^5$) taken together is azetidinyl, pyrrolidinyl, piperidinyl, piperazinyl, morpholinyl, homopiperidinyl, homopiperazinyl, or homomorpholinyl, and is substituted with 0-3 substituents selected from oxo, alkoxy, hydroxy and alkyl;
$R^6$ is hydrogen, or alkyl;
$R^7$ is hydrogen, or alkyl;
$R^8$ is hydrogen, alkyl, or cycloalkyl; and
$R^9$ is amino, alkylamino, or dialkylamino;
or a pharmaceutically acceptable salt thereof.

Another aspect of the invention is a compound of formula I where R$^1$ is phenyl substituted with 0-2 substituents selected from halo, alkyl, cyano, and nitro.

Another aspect of the invention is a compound of formula I where R$^1$ is phenyl.

Another aspect of the invention is a compound of formula I where R$^2$ is hydrogen.

Another aspect of the invention is a compound of formula I where R$^3$ is hydrogen.

Any scope of a substituent, including R$^1$, R$^2$, R$^3$, R$^4$, R$^5$, R$^6$, R$^7$, R$^9$, and R$^9$, can be used independently with the scope of any other instance of a substituent.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4 phenylcyclohexylamine, piperazine, potassium, sodium, tromethamine, and zinc.

The invention includes all stereoisomeric forms of the compounds, both mixtures and separated isomers. Mixtures of stereoisomers can be separated into individual isomers by methods known in the art.

Synthetic Methods

Standard chemistry known to those skilled in the art can be used to convert carboxylic acid B can be converted to Amides of Formula I (Scheme 1). Carboxylic acid B can be first activated using reagents such as carbonyl diimidazole to form the acyl imidazole, cyanuric fluoride to form the acyl fluoride, thionyl chloride to form the acyl chloride, or the like. Subsequent treatment of the resulting activated intermediates with a primary or secondary amine, or with ammonia, gives the Amides of Formula 1.

Alternatively, Amides of Formula 1 can be prepared from carboxylic acid A and primary or secondary amines using coupling reagents such as dicyclohexyl carbodiimide (DCC), 1-(3-dimethylaminopropyl)-3-ethylcarbodiimide hydrochloride (EDC), or the like. It is also common to run these reactions in the presence of 1H-benzo[d][1,2,3]triazol-1-ol (HOBt) and a weak base such as triethyl amine.

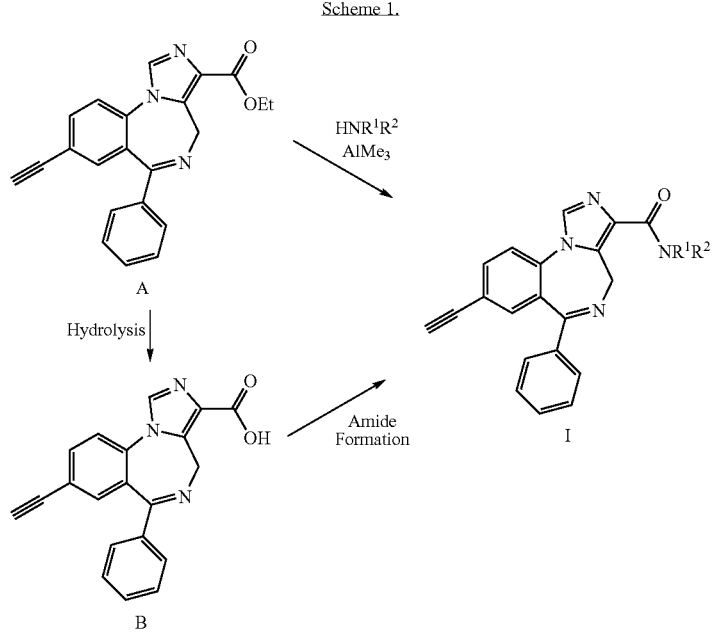

Scheme 1.

Amides of Formula I can be conveniently prepared directly from ethyl 8-ethynyl-6-phenyl-4H-benzo[f]imidazo[1,5-a][1,4]diazepine-3-carboxylate, A, by reaction with the appropriate amine in the presence of Lewis acids such as trimethyl aluminum (Scheme 1).

Alternatively, ester A can be hydrolyzed to carboxylic acid B which can then be converted to amides of Formula I using standard conditions. The hydrolysis of ester A can be accomplished using conditions such as sodium hydroxide or lithium hydroxide in solvents such as water, alcohol/water mixtures, THF/water mixtures, or the like. If organic co-solvents are used, these can be readily remove in vacuo. The resulting aqueous solution can then be made acidic to precipitate the carboxylic acid, B, which is filtered and dried. Alternatively, carboxylic acid B can be isolated from the acidified aqueous solution by extraction with solvents such as ethyl acetate, or the like.

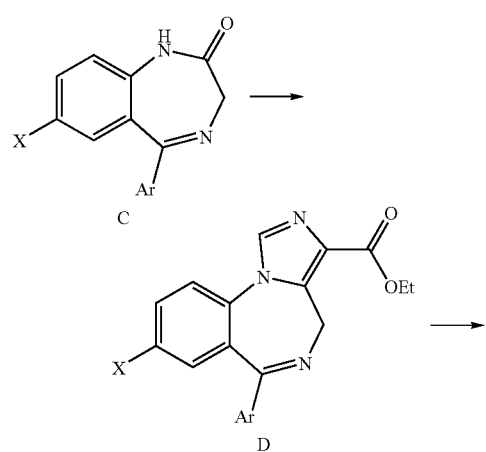

Scheme 2.

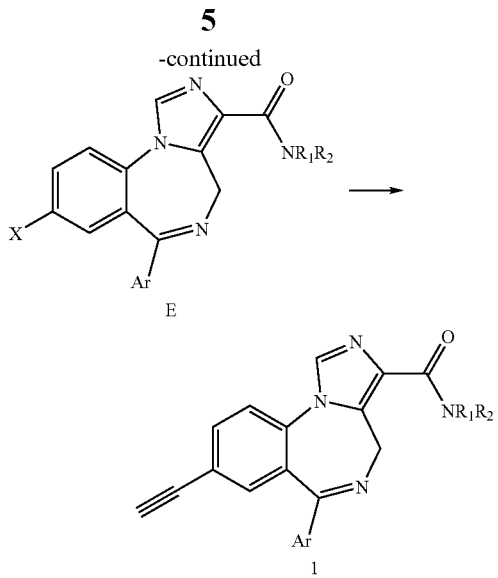

Alternatively, Amides of Formula 1 can be made by the procedures described in Scheme 2. Benzodiazepines, C, can be activated by reaction with reagents such as POCl$_3$, and then cyclized with reagents such as ethyl 2-isocyanoacetate to give the imidazole esters, D. Intermediates D can then converted to the amides, E, using the methods describe above in Scheme 1. Subsequent introduction of the acetylene group to the amides, E, using reagents such as TMS-acetylene and catalysts such as bis(triphenylphosphine)palladium(II) acetate provides the Compounds of Formula 1.

Biological Methods

Cell Line Generation and Transient Expression. In order to generate stable clonal lines expressing GABA$_A$ configurations containing α2β2γ2 subunits, HEK293 cells were transfected with 2 μg of the subunit, using the Invitrogen Lipofectamine PLUS protocol. The following DNA and vector were used for the stable transfection: α2 subunits in pIRES Neo2, β2 subunit in pIRES Hygro2, and a γ2 subunit in pIRES Puro2. Transfectants were selected with G418, Hygromycin B, and Puromycin antibiotics and cloned by limiting dilution. For transient expression, transfections were performed using the Amaxa transfection protocol and 2 μg DNA of the GABA$_A$ receptor subunit using Amaxa transfection protocol. Cells were used for experiments 24-72 hrs post transfection.

PatchXpress® 7000A Automated Parallel Patch-Clamp System. HEK293 cells stably expressing recombinant the rat GABA$_A$/α2β2γ2 configuration were harvested by a single DPBS wash followed by 0.025% Trypsin-EDTA treatment for one minute at room temperature. A 6-ml cell suspension (1.7×10$^5$ cells/ml) was centrifuged at 500 rpm for 60 s. The cell pellet was gently agitated, suspended in 150 μl extracellular saline buffer, and transferred to a 1.5-ml tube.

After manually placing the AVIVA Biosciences SealChip 16™ in the holder of the PatchXpress®, the SealChip16™ was automatically prepared for application of the cells. Intracellular solution containing (in mM) CsCl, 135; EGTA, 11; MgCl$_2$, 1; HEPES, 10; ATP, 5; GTP, 0.3 (pH 7.3 with CsOH, 290-300 mOsmol) was injected into the bottom of each chamber, and extracellular solution containing (in mM) NaCl, 140; KCl, 4; CaCl$_2$, 1.8; MgCl$_2$, 1; glucose, 10; HEPES, 10; ATP-K2, 5 (pH 7.4 with NaOH 305-310 mOsmol) was perfused into the top of the chambers through a 16-nozzle wash station. Throughout this period, the pressure controller maintained a positive pressure (+10 mmHg) from the intracellular side to keep the hole free of debris. Seal formation was achieved by a ramp increase in negative pressure from 0 to −35 mmHg at a rate of −3.5 mmHg/s every 10 s until a giga ohm seal was obtained and verified for 30 s.

Compounds were prepared from fresh DMSO stock and were transferred to a 96-well disposable glass insert compound plate for placement in the PatchXpress®. A full 10 point concentration-response curve for GABA was obtained for the GABA receptor cell line, from which an EC$_{20}$ was estimated. Test compounds were assayed for their ability to potentiate the current response by an EC$_{20}$ concentration of GABA. Each experiment began by two consecutive applications of GABA EC$_{20}$ alone. Following formation of a giga-ohm seal, patch chambers were perfused with extracellular saline for 60 s to remove excess cells from the well. Cells were then voltage-clamped to −60 mV for the duration of the experiment. After 60 s, 30 μl (10 μl/s over 3 s) of GABA EC$_{20}$ concentration, which elicited a GABA receptor-mediated inward Cl$^-$ current generally in the order of 200-300 pA in peak amplitude, was added to each chamber. The GABA EC$_{20}$ concentration was then washed out of the recording chamber after 5 s and washing with extracellular saline was continued for 60 s. After another 60 s, a second GABA EC$_{20}$ concentration was applied under the same paradigm. Only cells exhibiting stable baseline responses to GABA were included in data analysis. Following the second GABA EC$_{20}$ application, the lowest concentration of test compound in the presence of the GABA EC$_{20}$ concentration was similarly applied. Ascending concentrations of the test compound were applied successively to an individual well in the presence of the GABA EC$_{20}$ concentration.

Only cells meeting strict predetermined patch-clamp QC parameters, including seal resistance, membrane resistance, and holding current were included in data analysis. GABA current responses in the presence of test compound were measured and expressed as the mean of the initial control GABA EC$_{20}$ current responses. The peak current amplitude was measured using DataXpress/pCLAMP9 (Axon Instruments). Linear leak subtraction was performed off-line. The percent increase in the mean GABA EC$_{20}$ response produced by the test compound was plotted against compound concentration and fitted with a four-parameter logistic equation in ExcelFit from which the compound EC$_{50}$ (potency) and E$_{max}$ (efficacy) values were determined (Table 2).

TABLE 2

Functional activity of Amides of Formula I at rat GABA$_A$ α2β2γ2 Receptors.

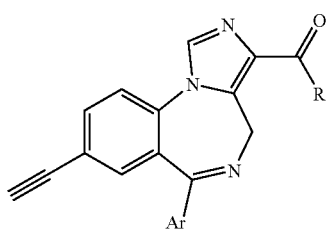

| Example | R | Ar | GABA$_A$ α2 EP EMAX (%) |
|---|---|---|---|
| 1 | —NEt2 | Ph | *** |
| 2 | —NHEt | Ph | ** |

TABLE 2-continued

| # | R | Ar | Emax |
|---|---|---|---|
| 3 | —NH2 | Ph | ** |
| 4 | —NH—CH$_2$CH$_2$—OMe | Ph | **** |
| 5 | —NH—CH$_2$CH$_2$OH | Ph | *** |
| 6 | —NH—CH$_2$CH$_2$—NMe$_2$ | Ph | ** |
| 7 | —NH—CH$_2$CO$_2$Et | Ph | ** |
| 8 | 1-(4-methyl)piperazine | Ph | ** |
| 9 | Morpholin-4-yl | Ph | *** |
| 10 | —NH-cPropyl | Ph | **** |
| 11 | —NH—CH$_2$-cPropyl | Ph | ** |
| 12 | —NH—CH$_2$—CH$_2$—OEt | Ph | ** |
| 13 | —NH—CHEt—CH$_2$—OMe | Ph | * |
| 14 | —NH—CH(cPr)—CH$_2$—OMe | Ph | * |
| 15 | —NH—CH(CH$_2$—OMe)$_2$ | Ph | * |
| 16 | —N(CH$_2$CH$_2$—OMe)$_2$ | Ph | * |
| 17 | —NH—CHMe—CH$_2$OMe | Ph | * |
| 18 | —NH—(CH$_2$)$_3$—OMe | Ph | *** |
| 19 | —NH—CH$_2$—CH$_2$—O-nPr | Ph | *** |
| 20 | —NH—CH$_2$CH$_2$—O-iPr | Ph | *** |
| 21 | 1-(4-pyrimidinyl)-piperazine | Ph | * |
| 22 | —NH—(CH$_2$)$_5$—NH— | Ph |  |
| 23 | —NH—(CH$_2$)$_2$—O—(CH$_2$)$_2$—NH— | Ph | * |
| 24 | —NH—(CH$_2$)$_2$—NMe—(CH$_2$)$_2$—NH— | Ph | ** |
| 25 | —NH—(CH$_2$)$_2$—S—(CH$_2$)$_2$—NH— | Ph | * |
| 26 | —NH—CH$_2$—CHEt—OH | Ph | * |
| 27 | (R)—NH—CH$_2$—CHMe—OH | Ph | * |
| 28 | (S)—NH—CH$_2$—CHMe—OH | Ph | ** |
| 29 | —NH—(CH$_2$)$_3$—OH | Ph | ** |
| 30 | —NH—(CH$_2$)$_5$—OH | Ph | ** |
| 31 | —NH—(CH$_2$)$_4$—OH | Ph | ** |
| 32 | —NH—(CH$_2$)$_2$—OAc | Ph | ** |
| 33 | —NH—CH$_2$CO$_2$H | Ph | *** |
| 34 | —NH—CH$_2$CH$_2$OMe | 2-F-Ph | ** |
| 35 | —NH—CH$_2$-2-Furyl | Ph | * |
| 36 | —NH—CH$_2$-2-tetrahydrofuryl | Ph | ** |
| 37 | —NH—CH$_2$CH$_2$—OMe | -2-Pyridyl | * |

200% < Emax < 300  *
300% < Emax < 400  **
400% < Emax < 500  ***
500% < Emax  ****

Pharmaceutical Composition and Methods of Use

The compounds of Formula I demonstrate GABA$_A$ α2 agonism. Agonism at these receptors correlates with efficacy for central nervous system disorders. As such, the compounds of Formula I can be useful for the treatment of these disorders and other aspects of the invention are compositions and methods of using the compounds to treat these conditions.

GABA modulators can be useful in the treatment of several central nervous system disorders including anxiety disorders such as panic disorder, agoraphobia, various phobias including social and animal phobias, obsessive-compulsive disorder, general anxiety disorder, substance-induced anxiety disorders, attention deficit disorders, stress disorders including acute and post-traumatic stress disorders, neuroses, convulsions, migraine, depressive, manic, and bipolar disorders, dysthymic disorder, cyclothymic disorder, and psychotic disorders including schizophrenia. These modulators are may also be useful it the treatment of cognitive disorders in, for example, schizophrenia, depression, and Alzheimer's disease.

The compounds of this invention are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 1 mg, 10 mg, 100 mg, 250 mg, 500 mg, and 1000 mg. Liquid compositions are generally in a unit dosage range of 1-100 mg/mL. Some examples of liquid dosage units are 1 mg/mL, 10 mg/mL, 25 mg/mL, 50 mg/mL, and 100 mg/mL. Generally, the dosage unit will be in a unit range similar to agents of that class used clinically, for example diazepam.

The invention encompasses all conventional modes of administration; oral and parenteral methods are preferred. Generally, the dosing regimen will be similar to agents of that class used clinically, for example diazepam. Typically, the daily dose will be 0.01-100 mg/kg body weight daily. Generally, more compound is required orally and less parenterally. The specific dosing regime, however, should be determined by a physician using sound medical judgement.

DESCRIPTION OF SPECIFIC EMBODIMENTS

Intermediate B

8-Ethynyl-6-phenyl-4H-benzo[f]imidazo[1,5-a][1,4]diazepine-3-carboxylic acid, B. Ethyl 8-ethynyl-6-phenyl-4H-benzo[f]imidazo[1,5-a][1,4]diazepine-3-carboxylate, A, (1 g, 2.81 mmol) and lithium hydroxide hydrate (250 mg, 5.96 mmol) were dissolved in THF (20 ml) and water (5 ml). The mixture was stirred 18 hr at room temperature. The resulting light brown solution was concentrated in vacuo. The residue was dissolved in water (20 ml) and the solution cooled in an ice bath for 15 min. By syringe, 12N HCl (0.5 ml, 6 mmol) was added drop-wise to give a white precipitate, which was filtered, washed with water, and air dried. After further drying under high vacuum, the product was obtained as a white powder (885 mg, 96%).

LCMS (5-95% acetonitrile/water/10 mM ammonium acetate; 4 ml/min, 3 min gradient, Phenomenex Luna C18 4.6×50 mm 10 u, 254 nm) Rt=1.78 min, 100%, ES$^+$=328, 329.

HPLC (10-90% methanol/water/0.1% TFA; 2.5 ml/min, 15 min gradient, Phenomenex LUNA Phenyl-Hexyl 4.6×150 mm, 254 nm): Rt=8.90 min, 97.4%.

Example 1

N,N-Diethyl-8-ethynyl-6-phenyl-4H-benzo[f]imidazo[1,5-a][1,4]diazepine-3-carboxamide. 8-Ethynyl-6-phenyl-4H-benzo[f]imidazo[1,5-a][1,4]diazepine-3-carboxylic acid (98 mg, 0.3 mmol) was dissolved in DMF (6 ml) and then 1H-benzo[d][1,2,3]triazol-1-ol (40.5 mg, 0.3 mmol), N1-((ethylimino)methylene)-N3,N3-dimethylpropane-1,3-diamine hydrochloride (57.5 mg, 0.3 mmol), and triethylamine (0.042 ml, 0.3 mmol) were added. The solution was stirred for 15 min and then diethylamine (0.031 ml, 0.3 mmol) was added. The solution was stirred at room temperature for 16 hr and then concentrated in vacuo. The residue was dissolved in ethyl acetate (8 ml), extracted with water (2×3 ml), and dried with brine (2×2 ml). The ethyl acetate was removed with a nitrogen stream. The residue was dissolved in methylene chloride and applied to a silica gel column. The product was eluted with ethyl acetate. Upon concentrating the product fractions, the product solidified as a white powder (69 mg, 60.1%).

LCMS (5-95% acetonitrile/water/10 mM ammonium acetate; 4 ml/min, 3 min gradient, Phenomenex Luna C18 4.6×50 mm 10 u, 254 nm) Rt=2.00 min, 100%, ES$^+$=383, 384.

HPLC (10-90% methanol/water/0.1% TFA; 2.5 ml/min, 15 min gradient, Phenomenex Onyx C18 4.6×50 mm, 254 nm): Rt=7.44 min, 94.9%.

Example 2

N-Ethyl-8-ethynyl-6-phenyl-4H-benzo[f]imidazo[1,5-a][1,4]diazepine-3-carboxamide dihydrochloride. 8-Ethynyl-6-phenyl-4H-benzo[f]imidazo[1,5-a][1,4]diazepine-3-carboxylic acid (82 mg, 0.251 mmol) was dissolved in DMF (6 ml) and then N1-((ethylimino)methylene)-N3,N3-dimethylpropane-1,3-diamine hydrochloride (48 mg, 0.251 mmol), 1H-benzo[d][1,2,3]triazol-1-ol (33.8 mg, 0.251 mmol), and triethylamine (70 µL, 0.501 mmol) were added. The solution was stirred for 15 min and then ethylamine hydrochloride (20.4 mg, 0.251 mmol) was added. The solution was stirred at room temperature for 3 days. The DMF was removed in vacuo. The residue was dissolved in ethyl acetate and extracted with water twice, then dried with brine. The ethyl acetate layer was then condensed with a stream of nitrogen, and dried in vacuo. The residue was dissolved in methylene chloride, and applied to a silica gel column. The product was eluted with ethyl acetate. The product fractions were concentrated in vacuo. The oily residue was dissolved in acetonitrile and several drops of concentrated HCl were added to give the HCl salt. The acetonitrile was removed in vacuo and the HCl salt was dried under high vacuum to give a yellow powder (75 mg, 77%).

$^1$H NMR (400 MHz, MeOD) δ ppm 1.20 (t, J=7.30 Hz, 3H) 3.40 (q, J=7.30 Hz, 2H) 3.84 (s, 1H) 7.56 (d, J=2.01 Hz, 1H) 7.61-7.71 (m, 4H) 7.82-7.92 (m, 1H) 8.01-8.08 (m, 1H) 8.09-8.16 (m, 1H) 8.41 (s, 1H).

LCMS (5-95% acetonitrile/water/10 mM ammonium acetate; 4 ml/min, 3 min gradient, Phenomenex Luna C18 4.6×50 mm 10 u, 254 nm) Rt=1.96 min, 100%, ES$^+$=355, 356.

HPLC (10-90% methanol/water/0.1% TFA; 2.5 ml/min, 8 min gradient, Zorbax SB-C18 4.6×75 mm S5, 254 nm): Rt=8.69 min, 99.1%.

Example 3

8-Ethynyl-6-phenyl-4H-benzo[f]imidazo[1,5-a][1,4]diazepine-3-carboxamide. A mixture of 8-ethynyl-6-phenyl-4H-benzo[f]imidazo[1,5-a][1,4]diazepine-3-carboxylic acid (1 g, 3.05 mmol) and pyridine (0.494 mL, 6.11 mmol) in THF (25 mL) was stirred as 2,4,6-trifluoro-1,3,5-triazine (0.825 mL, 9.16 mmol) was added. The mixture was stirred for 16 hr. The reaction was diluted with ethyl acetate and the mixture extracted with water and dried with brine. The organic layer was concentrated to a pink solid. Ammonia (0.5 M in dioxane, 20 mL, 10.00 mmol) was added to the pink solid and the solution was stirred for 2 hr to give a precipitate. The precipitate was filtered and washed with water. The solid was stirred in hot ethyl acetate. The mixture cooled and filtered. The pink powder was stirred in hot 95% ethanol (25 ml) and the mixture cooled in the freezer. The solid was filtered and air dried to a pink powder (0.69 g, 69.2%).

$^1$H-NMR (CDCl$_3$): δ 3.15 (s, 1H), 4.03 (bd, 1H), 5.37 (bs, 1H), 6.20 (bd, 1H), 6.97 (bs, 1H), 7.35 (t, 2H), 7.43 (t of t, 1H), 7.48-7.50 (m, 2H), 7.52 (d, 1H), 7.56 (m, 1H), 7.74 (d of d, 1H), 7.84 (s, 1H).

LCMS (5-95% acetonitrile/water/10 mM ammonium acetate; 4 ml/min, 3 min gradient, Phenomenex Luna C18 4.6×50 mm 10 u, 254 nm) Rt=1.85 min, ES$^+$=325, ES$^-$=327, 328.

HPLC (10-90% methanol/water/0.1% TFA; 2.5 ml/min, 15 min gradient, Phenomenex Gemini C18 4.6×150 mm S5, 254 nm): Rt=7.540 min, 95.0%.

HPLC (10-90% methanol/water/0.1% TFA; 2.5 ml/min, 15 min gradient, Phenomenex LUNA Phenyl-Hex 4.6×150 mm S5, 254 nm): Rt=8.719 min, 96.1%.

Example 4

8-Ethynyl-N-(2-methoxyethyl)-6-phenyl-4H-benzo[f]imidazo[1,5-a][1,4]diazepine-3-carboxamide Dihydrochloride Method 1 (Acyl Fluoride Method)

A mixture of 8-ethynyl-6-phenyl-4H-benzo[f]imidazo[1,5-a][1,4]diazepine-3-carboxylic acid (2 g, 6.11 mmol) and pyridine (0.59 mL, 7.33 mmol) in THF (50 mL) was stirred as 2,4,6-trifluoro-1,3,5-triazine (1.1 mL, 12.2 mmol) was added. The mixture was stirred for 18 hr. The suspension was concentrated in vacuo and diluted with ethyl acetate. The mixture was extracted twice with cold water and dried with brine. The ethyl acetate layer was concentrated in vacuo. The yellow residue was diluted with THF (50 mL) and 2-methoxyethylamine (1.99 mL, 22.9 mmol) was added. The mixture was stirred for 15 min. The THF was removed in vacuo and the residue dissolved in ethyl acetate/water. The ethyl acetate layer was separated, washed with water, dried with brine, and concentrated in vacuo to a red solid (2.35 g, 100%). The crude material was purified by silica gel chromatography using ethyl acetate as the eluent to give the product as a colorless solid. The solid was dissolved in acetonitrile (50 ml) and excess 12N HCl was added with stirring. The solution was cooled in an ice bath for 20 min to give the di-HCl salt as a white precipitate that was filtered and air dried (2.07 g, 80%).

$^1$H NMR (400 MHz, DMSO-d6) δ ppm 3.25 (s, 3H) 3.43 (s, 4H) 4.37 (s, 1H) 4.44 (s, 1H) 5.94 (s, 1H) 7.41 (s, 1H) 7.49-7.57 (m, 4H) 7.62 (m, 1H) 8.00 (s, 2H) 8.15 (s, 1H) 8.50 (s, 1H).

HPLC (10-90% methanol/water/0.1% TFA; 2.5 ml/min, 15 min gradient, Phenomenex Gemini C18 4.6×150 mm S5, 254 nm): Rt=8.44 min, 92.8%.

HPLC (10-90% methanol/water/0.1% TFA; 2.5 ml/min, 15 min gradient, Phenomenex LUNA Phenyl-Hex 4.6×150 mm S5, 254 nm): Rt=9.82 min, 94.1%.

Method 2 (Trimethylaluminum Method)

A solution of 2-methoxyethanamine (0.15 mL, 1.69 mmol) in methylene chloride (5 mL) was stirred under nitrogen at room temperature as trimethylaluminum 2M in hexane (0.84 mL, 1.69 mmol) was slowly added. The mixture was stirred for 15 min and then ethyl 8-ethynyl-6-phenyl-4H-benzo[f]imidazo[1,5-a][1,4]diazepine-3-carboxylate (500 mg, 1.41 mmol) was added. The solution was heated in a warm (~40° C.) water bath for 16 hr. In a separate flask, trimethylaluminum 2M in hexane (0.84 mL, 1.69 mmol) was added to 2-methoxyethanamine (0.15 mL, 1.69 mmol), stirred for 15 min. This solution was then added to the reaction mixture. Heating and stirring were continued for 1 day. The solution was concentrated and the residue dissolved in methanol. The mixture was filtered and the filtrate concentrated. The residue was dissolved in ethyl acetate and applied to a silica gel column. The product was eluted with ethyl acetate and the product fractions concentrated to give a clear oil. The clear oil foamed and solidified under high vacuum to give the product as a white solid (0.39 g, 71.4%).

Method 3 (CDI Method)

A mixture of 8-ethynyl-6-phenyl-4H-benzo[f]imidazo[1,5-a][1,4]diazepine-3-carboxylic acid (5 g, 15.27 mmol) and carbonyl diimidazole (3.22 g, 19.86 mmol) in THF (100 mL) was heated to reflux for 1 hr to give a clear solution. By syringe, 2-methoxyethanamine (2.66 mL, 30.5 mmol) was added to the hot solution and the reflux was continued for 1 hr. The solution was cooled and concentrated. The residue was dissolved in ethyl acetate. The solution was washed twice with water, twice with saturated Na2CO3, and dried with brine. The ethyl acetate solution was concentrated.

The residue was dissolved in methylene chloride and applied to a silica gel column. The product was eluted with ethyl acetate. The product fractions were concentrated to give a foam that solidified. The foam was dissolved in ethyl acetate and 4M HCl in dioxane (10 mL, 40.0 mmol) was added slowly with stirring to give a white precipitate. The mixture was stirred 18 hr overnight. The white precipitate was filtered and air dried. The white powder was dried under high vacuum at 80° C. for 2 hr to give the di-hydrochloride product as a white powder (7.00 g, 96%).

Method 4 (Di-HCl Salt Formation)

8-Ethynyl-N-(2-methoxyethyl)-6-phenyl-4H-benzo[f]imidazo[1,5-a][1,4]diazepine-3-carboxamide dihydrochloride (prepared from the free base). (Z)-8-ethynyl-N-(2-methoxyethyl)-6-phenyl-4H-benzo[f]imidazo[1,5-a][1,4]diazepine-3-carboxamide (5.17 g) prepared by the methods above, was dissolved in acetone (100 ml) and filtered into a 250 ml beaker. The solution was stirred as 12N HCl (2.58 ml, 30.9 mmol) was added from a syringe. Initially, a white precipitate formed and then formed a partial gum. After stirring at room temperature for 2 hr, all of the material was a white powder. The white powder was filtered, washed with acetone, and air dried. The material was then dried for 4 hr at 100° C. under high vacuum to give the di-HCl salt as a white powder (4.75 g, 77%).

$^1$H-NMR (400 MHz, d6-DMSO): δ 3.25 (s, 3H), 3.42 (s, 4H), 4.37 (bs, 1H), 4.42 (s, 1H), 5.92 (bs, 1H) 7.41 (s, 1H), 7.47-7.52 (m, 4H), 7.58-7.60 (m, 1H), 7.97 (s, 2H), 8.11 (bt, 1H, disappears upon adding D$_2$O), 8.46 (s, 1H), 8.87 (bs, 2H).

HPLC (Gemini S5 4.6×150 mm C18, 5-100% H$_2$0/acetonitrile/10 mM NH$_4$OAc, pH=6.8, 1 ml/min, 18 min method, 254 wavelength): Rt=11.18 min, 100%.

Example 5

8-Ethynyl-N-(2-hydroxyethyl)-6-phenyl-4H-benzo[f]imidazo[1,5-a][1,4]diazepine-3-carboxamide. 8-Ethynyl-6-phenyl-4H-benzo[f]imidazo[1,5-a][1,4]diazepine-3-carboxylic acid (1.071 g, 3.27 mmol), 1,1'-carbonyl diimidazole (0.637 g, 3.93 mmol) and 2-aminoethanol (0.395 mL, 6.54 mmol) were reacted in THF (30 mL) by the method shown in Example 4, Method 3. The reaction produced white precipitate. The reaction was cooled and the precipitate was filtered, washed with ethyl acetate, and air dried to a white powder (0.911 g, 75%)

$^1$H NMR (400 MHz, DMSO-D6) δ ppm 3.27-3.37 (m, 3H) 3.49 (q, J=5.96 Hz, 2H) 4.07 (d, J=12.34 Hz, 1H) 4.36 (s, 1H) 4.75 (t, J=5.41 Hz, 1H) 5.94 (d, J=12.34 Hz, 1H) 7.38-7.50 (m, 6H) 7.85-7.93 (m, 2H) 8.00 (t, J=5.92 Hz, 1H) 8.38 (s, 1H).

MS: ES$^+$=370.63, 371.64.

HPLC (5-95% acetonitrile/water/10 mM ammonium acetate; 1 ml/min, 15 min gradient, Gemini C18 4.6×150 mm S5, 254 nm): Rt=10.78 min, 100%.

HPLC (5-95% acetonitrile/water/10 mM ammonium acetate; 1 ml/min, 15 min gradient, Xbridge C18 4.6×150 mm S3.5, 254 nm): Rt=10.62 min, 100%.

Example 6

N-(2-(Dimethylamino)ethyl)-8-ethynyl-6-phenyl-4H-benzo[f]imidazo[1,5-a][1,4]diazepine-3-carboxamide. 8-Ethynyl-6-phenyl-4H-benzo[f]imidazo[1,5-a][1,4]diazepine-3-carboxylic acid (5 g, 15.27 mmol), 1,1'-carbonyl diimidazole (3.22 g, 19.86 mmol), and N1,N1-dimethylethane-1,2-diamine (3.35 mL, 30.5 mmol) were reacted in THF (75 mL) by the method shown in Example 4, Method 3. The solution was concentrated. The residue was dissolved in ethyl acetate, extracted twice with water, and dried with brine. The ethyl acetate layer was concentrated. The residue was dissolved in ethyl acetate (75 ml) and 4M HCl in dioxane (14 mL, 56.0 mmol) was added slowly from a syringe to give a precipitate. The mixture was stirred 16 hr overnight. The mixture was filtered, and the precipitate was washed with ethyl acetate and acetone. The powder dried at 80° C. under high vacuum for 2 hr to give a pale yellow powder (5.42 g, 70.0%).

$^1$H NMR (400 MHz, DMSO-d6) δ ppm 2.78 (s, 3H) 2.79 (s, 3H) 3.23 (q, J=6.04 Hz, 2H) 3.64 (q, J=5.79 Hz, 2H) 4.42 (br. s., 1H) 4.46 (s, 1H) 5.95 (br. s., 1H) 7.41 (s, 1H) 7.50-7.60 (m, 4H) 7.63 (t, J=7.18 Hz, 1H) 7.97-8.05 (m, 2H) 8.56 (s, 1H) 8.63 (t, J=5.92 Hz, 1H) 10.65 (br. s., 1H) 12.0 (br. s., 2H).

LCMS (5-95% acetonitrile/water/10 mM ammonium acetate; 5 ml/min, 4 min gradient, Xbridge C18 4.6×50 mm 5 u, 254 nm) Rt=1.56 min, 100%, ES$^+$=398, 399, ES$^-$=396, 397.

HPLC (5-95% acetonitrile/water/10 mM ammonium acetate; 1 ml/min, 15 min gradient, Xterra C18 4.6×150 mm S3.5, 254 nm): Rt=8.91 min, 98.8%.

HPLC (5-95% acetonitrile/water/10 mM ammonium acetate; 1 ml/min, 10 min gradient, Xbridge Phenyl 4.6×150 mm S3.5, 254 nm): Rt=12.39 min, 98.92%.

Example 7

Ethyl 2-(8-ethynyl-6-phenyl-4H-benzo[f]imidazo[1,5-a][1,4]diazepine-3-carboxamido)acetate. 8-Ethynyl-6-phenyl-4H-benzo[f]imidazo[1,5-a][1,4]diazepine-3-carboxylic acid (103 mg, 0.315 mmol), 1,1'-carbonyl diimidazole (63.8 mg, 0.393 mmol), and ethyl 2-aminoacetate hydrochloride (43.9 mg, 0.315 mmol) in THF (10 ml) and triethylamine (0.132 ml, 0.944 mmol) by the method shown in Example 4, Method 3. The mixture was concentrated in vacuo. The residue was purified by silica gel chromatography using ethyl acetate as the eluent to give the product as a white solid (44 mg, 34%).

$^1$H NMR (400 MHz, chloroform-d) δ ppm 1.27 (t, J=7.05 Hz, 3H) 3.14 (s, 1H) 4.04 (d, J=12.09 Hz, 1H) 4.16 (d, J=5.04 Hz, 1H) 4.21 (m, 3H) 6.19 (d, J=12.59 Hz, 1H) 7.31-7.39 (m, 2H) 7.39-7.46 (m, 1H) 7.47-7.58 (m, 5H) 7.74 (dd, J=8.31, 1.76 Hz, 1H) 7.84 (s, 1H).

LCMS (Phenomenex LUNA C18 4.6×50 mm S10, 4 ml/min, 3 min gradient): R$_t$=2.40 min, 96.3%, (M+H)$^+$=413, 414.

HPLC (10-90% methanol/water/0.1% TFA; 2.5 ml/min, 15 min gradient, Phenomenex LUNA Phenyl-Hex 4.6×150 mm S5, 254 nm): Rt=10.25 min, 93.4%.

Example 8

(8-Ethynyl-6-phenyl-4H-benzo[f]imidazo[1,5-a][1,4]diazepin-3-yl)(4-methylpiperazin-1-yl)methanone. 8-Ethynyl- 6-phenyl-4H-benzo[f]imidazo[1,5-a][1,4]diazepine-3-carboxylic acid was converted to the acyl fluoride as in Example 4, Method 1. The 8-ethynyl-6-phenyl-4H-benzo[f]imidazo [1,5-a][1,4]diazepine-3-carbonyl fluoride (110 mg, 0.334 mmol)] was stirred with 1 ml saturated sodium carbonate as 1-methylpiperazine (37.0 µL, 0.334 mmol) was added. The mixture was stirred 2 days over the weekend. The aqueous layer was removed with a Pasteur pipette. The ethyl acetate layer was applied to a silica gel column and the product eluted with a step gradient of 20-60% methanol/ethyl acetate. The product fractions were concentrated to give the product as a light brown powder (96.5 mg, 69.1%).

1H-NMR (400 MHz, CDCl3): δ 2.43 (s, 3H), 2.67 (bs, 4H), 3.14 (s, 1H), 3.88 (bs, 2H), 4.07 (d, 1H), 4.19 (bs, 2H), 5.83 (d, 1H), 7.24 s, 1H), 7.36 (t, 2H), 7.41-7.45 (m, 1H), 7.47-7.54 (m, 4H), 7.73 (dd, 1H), 7.83 (s, 1H).

LCMS (5-95% acetonitrile/water/10 mM ammonium acetate; 4 ml/min, 3 min gradient, Phenomenex Luna C18 4.6×50 mm 10 u, 254 nm): Rt=2.00 min, 100%, ES$^+$=410, 411.

HPLC (5-95% acetonitrile/water/10 mM ammonium acetate; 1 ml/min, 15 min gradient, Xterra C18 4.6×150 mm S3.5, 254 nm): Rt=8.87 min, 99.4%.

HPLC (5-95% acetonitrile/water/10 mM ammonium acetate; 1 ml/min, 15 min gradient, Xbridge C18 4.6×150 mm S3.5, 254 nm): Rt=9.14 min, 98.6%.

Example 9

8-Ethynyl-6-phenyl-4H-benzo[f]imidazo[1,5-a][1,4]diazepin-3-yl)(morpholino)methanone. 8-Ethynyl-6-phenyl-4H-benzo[f]imidazo[1,5-a][1,4]diazepine-3-carboxylic acid was converted to the acyl fluoride as in Example 4, Method 1. The 8-ethynyl-6-phenyl-4H-benzo[f]imidazo[1,5-a][1,4]diazepine-3-carbonyl fluoride (110 mg, 0.334 mmol)] was stirred with 1 ml saturated sodium carbonate as morpholine (29.1 µL, 0.334 mmol) was added. The mixture was stirred 2 days over the weekend. The aqueous layer was removed with a pasteur pipette. The ethyl acetate layer was applied to a silica gel column and the product eluted with a step gradient of 0-20% methanol/ethyl acetate. The product fractions were concentrated to give the product (83.7 mg, 61.9%).

$^1$H NMR (400 MHz, chloroform-d) δ ppm 2.30 (br. s., 4H) 3.20 (s, 1H) 3.74 (br. s., 4H) 4.20 (d, J=13.60 Hz, 1H) 5.97 (d, J=13.35 Hz, 1H) 7.46 (t, J=7.55 Hz, 2H) 7.53-7.65 (m, 5H) 7.84 (dd, J=8.44, 1.89 Hz, 1H) 7.92 (s, 1H).

LCMS (10-90% methanol/water/0.1% TFA; 4 ml/min, 3 min gradient, Phenomenex Luna C18 4.6×50 mm S10, 254 nm): Rt=2.30 min, 100%, ES$^+$=397, 398.

HPLC (5-95% acetonitrile/water/10 mM ammonium acetate; 1 ml/min, 15 min gradient, Xterra C18 4.6×150 mm S3.5, 254 nm): Rt=9.91 min, 100%.

HPLC (5-95% acetonitrile/water/10 mM ammonium acetate; 1 ml/min, 15 min gradient, Xbridge C18 4.6×150 mm S3.5, 254 nm): Rt=9.64 min, 99.7%.

Example 10

N-Cyclopropyl-8-ethynyl-6-phenyl-4H-benzo[f]imidazo [1,5-a][1,4]diazepine-3-carboxamide. This compound was prepared from 8-ethynyl-6-phenyl-4H-benzo[f]imidazo[1,5-a][1,4]diazepine-3-carboxylic acid and cyclopropanamine by the method shown in Example 1. The crude material was applied to a silica gel column and the product was eluted with a step gradient of ethyl acetate/methylene chloride (1:4, 1:1, then 1:0). The product fractions were concentrated to give the product as a clear oil (69 mg, 63%).

1H-NMR (400 MHz, CDCl3): δ 0.58-0.62 (m, 2H), 0.77-0.82 (m, 2H), 1.23 (s, 1H) 2.81-2.87 (m, 1H), 3.16 (s, 1H), 4.07 (bd, 1H), 6.27 (bd, 1H), 7.37 (t, 3H), 7.45 (t, 1H), 7.52-7.58 (m, 4H), 7.77 (dd, 1H), 7.99 (s, 1H).

LCMS (10-90% methanol/water/0.1% TFA; 4 ml/min, 3 min gradient, Phenomenex Luna C18 4.6×50 mm S10, 254 nm) Rt=2.36 min, 100%, ES$^+$=367, 368.

HPLC (5-95% acetonitrile/water/10 mM ammonium acetate; 1 ml/min, 15 min gradient, Xterra C18 4.6×150 mm S3.5, 254 nm): Rt=10.88 min, 98.8%.

HPLC (5-95% acetonitrile/water/10 mM ammonium acetate; 1 ml/min, 15 min gradient, Xbridge C18 4.6×150 mm S3.5, 254 nm): Rt=10.49 min, 98.5%.

Example 11

N-Cyclopropyl-8-ethynyl-6-phenyl-4H-benzo[f]imidazo [1,5-a][1,4]diazepine-3-carboxamide. This compound was prepared from 8-ethynyl-6-phenyl-4H-benzo[f]imidazo[1,5-a][1,4]diazepine-3-carboxylic acid (100 mg, 0.305 mmol), carbonyl diimidazole (99 mg, 0.611 mmol), and cyclopropylethanamine (0.5 ml, 0.305 mmol) in THF (4 mL) via the method shown in Example 4, Method 3. The crude product was purified on a silica gel column using a gradient of ethyl acetate/methylene chloride (30-100%) as the eluent. The product fractions were concentrated to give a white solid. The material was converted to the HCl salt (8 mg).

1H-NMR (400 MHz, d6-DMSO) 68835-021_10_DPX400A: δ 0.22 (d, 2H), 0.38 (d, 2H), 1.02 (bt, 1H), 3.12 (bt, 2H), 4.44 (bs, 1H), 4.46 (s, 1H), 5.95 (bs, 1H), 7.41 (s, 1H), 7.51 (m, 4H), 7.85 (bt, 1H), 8.02 (s, 2H), 8.36 (bt, 1H), 8.56 (s, 1H).

LCMS (10-90% methanol/water/0.1% TFA; 4 ml/min, 3 min gradient, Phenomenex Luna C18 4.6×50 mm S10, 254 nm) Rt=2.56 min, 100%, ES$^+$=381, 382.

HPLC (5-95% acetonitrile/water/10 mM ammonium acetate; 1 ml/min, 15 min gradient, Xterra C18 4.6×150 mm S3.5, 254 nm): Rt=11.93 min, 99.0%.

HPLC (5-95% acetonitrile/water/10 mM ammonium acetate; 1 ml/min, 15 min gradient, Xbridge C18 4.6×150 mm S3.5, 254 nm): Rt=11.58 min, 99.2%.

Example 12

N-(2-Ethoxyethyl)-8-ethynyl-6-phenyl-4H-benzo[f]imidazo[1,5-a][1,4]diazepine-3-carboxamide dihydrochloride. 8-Ethynyl-6-phenyl-4H-benzo[f]imidazo[1,5-a][1,4]diazepine-3-carboxylic acid was converted to the acyl fluoride as in Example 4, Method 1. A solution of 8-ethynyl-6-phenyl-4H-benzo[f]imidazo[1,5-a][1,4]diazepine-3-carbonyl fluoride (0.100 g, 0.305 mmol) in ethyl acetate (5 mL) was stirred as 2-ethoxyethanamine (0.096 mL, 0.915 mmol) (5 drops) was added. The solution was stirred for 1 hr. The reaction solution was extracted twice with water and dried with brine. The ethyl acetate solution was applied to a silica gel column and the product eluted with ethyl acetate. The product was concentrated in to give a foam that solidified to a pink solid (98.3 mg, 81%).

$^1$H NMR (400 MHz, chloroform-D) δ ppm 1.18 (t, J=7.05 Hz, 3H) 3.15 (s, 1H) 3.49 (q, J=6.88 Hz, 3H) 3.54 (s, 3H) 3.62 (s, 1H) 4.06 (d, J=12.34 Hz, 1H) 6.25 (d, J=12.59 Hz, 1H) 7.36 (t, J=7.43 Hz, 2H) 7.42-7.49 (m, 2H) 7.49-7.57 (m, 4H) 7.75 (dd, J=8.31, 1.76 Hz, 1H) 7.88 (s, 1H).

LCMS (5-95% acetonitrile/water/10 mM ammonium acetate; 2 ml/min, 4 min gradient, Xbridge C18 4.6×50 mm 10 u, 254 nm) Rt=1.83 min, 100%, ES$^+$=399, 400.

HPLC (5-95% acetonitrile/water/10 mM ammonium acetate; 1 ml/min, 15 min gradient, Gemini C18 4.6×150 mm S5, 254 nm): Rt=13.20 min, 99.4%.

HPLC (5-95% acetonitrile/water/10 mM ammonium acetate; 1 ml/min, 15 min gradient, Xbridge C18 4.6×150 mm S3.5, 254 nm): Rt=12.62 min, 99.3%.

Example 13

8-Ethynyl-N-(1-methoxybutan-2-yl)-6-phenyl-4H-benzo[f]imidazo[1,5-a][1,4]diazepine-3-carboxamide. This compound was prepared in a manner similar to Example 12 using 8-ethynyl-6-phenyl-4H-benzo[f]imidazo[1,5-a][1,4]diazepine-3-carbonyl fluoride (0.100 g, 0.305 mmol) and 1-methoxybutan-2-amine (0.106 mL, 0.915 mmol). A solution of the product in ethyl acetate was applied to a silica gel column and the product eluted with ethyl acetate. The product fractions were concentrated to give a pink resin (118.7 mg, 94%).

$^1$H NMR (400 MHz, chloroform-D) δ ppm 0.94 (d, J=4.03 Hz, 3H) 1.58 (s, 1H) 2.15 (s, 3H) 3.29-3.41 (m, 3H) 3.46 (s, 1H) 4.07 (s, 1H) 7.24 (s, 1H) 7.39 (t, J=7.55 Hz, 2H) 7.44-7.53 (m, 1H) 7.54-7.64 (m, 3H).

LCMS (5-95% acetonitrile/water/10 mM ammonium acetate; 2 ml/min, 4 min gradient, Xbridge C18 4.6×50 mm 10 u, 254 nm) Rt=2.04 min, 100%, ES$^+$=413, ES$^-$=411, 412.

HPLC (5-95% acetonitrile/water/10 mM ammonium acetate; 1 ml/min, 15 min gradient, Gemini C18 4.6×150 mm S5, 254 nm): Rt=13.90 min, 99.8%.

HPLC (5-95% acetonitrile/water/10 mM ammonium acetate; 1 ml/min, 15 min gradient, Xbridge C18 4.6×150 mm S3.5, 254 nm): Rt=13.14 min, 95.1%.

Example 14

N—((R)-1-Cyclopropyl-2-methoxyethyl)-8-ethynyl-6-phenyl-4H-benzo[f]imidazo[1,5-a][1,4]diazepine-3-carboxamide. This compound was prepared in a manner similar to Example 12 using 8-ethynyl-6-phenyl-4H-benzo[f]imidazo[1,5-a][1,4]diazepine-3-carbonyl fluoride (0.100 g, 0.305 mmol) and (R)-1-cyclopropyl-2-methoxyethanamine hydrochloride (92 mg, 0.610 mmol). A solution of the product in ethyl acetate was applied to a silica gel column and the product eluted with ethyl acetate. The product fractions were concentrated to give a pink resin solidified on standing (72.1 mg, 55.7%).

$^1$H NMR (400 MHz, chloroform-d) δ ppm 0.22-0.34 (m, 1H) 0.43 (d, J=7.05 Hz, 1H) 0.48 (d, J=19.39 Hz, 2H) 1.08 (br. s., 1H) 3.17 (s, 1H) 3.33-3.36 (m, 3H) 3.47-3.59 (m, 3H) 4.10 (d, 1H) 6.30 (d, 1H) 7.39 (t, J=7.55 Hz, 2H) 7.43-7.51 (m, 1H) 7.53-7.63 (m, 5H) 7.79 (d, J=8.06 Hz, 1H) 8.07 (br. s., 1H).

LCMS (5-95% acetonitrile/water/10 mM ammonium acetate; 2 ml/min, 4 min gradient, Xbridge C18 4.6×50 mm 10 u, 254 nm) Rt=2.18 min, 100%, ES$^+$=425, 426, ES$^-$=423.

HPLC (5-95% acetonitrile/water/10 mM ammonium acetate; 1 ml/min, 15 min gradient, Gemini C18 4.6×150 mm S5, 254 nm): Rt=14.08 min, 100%.

HPLC (5-95% acetonitrile/water/10 mM ammonium acetate; 1 ml/min, 15 min gradient, Xbridge C18 4.6×150 mm S3.5, 254 nm): Rt=13.52 min, 97.7%.

Example 15

N-(1,3-Dimethoxypropan-2-yl)-8-ethynyl-6-phenyl-4H-benzo[f]imidazo[1,5-a][1,4]diazepine-3-carboxamide. This compound was prepared in a manner similar to Example 12 using 8-ethynyl-6-phenyl-4H-benzo[f]imidazo[1,5-a][1,4]diazepine-3-carbonyl fluoride (0.100 g, 0.305 mmol), 1,3-dimethoxypropan-2-amine hydrochloride (95 mg, 0.610 mmol), and saturated aqueous sodium (1 ml). A solution of the product in ethyl acetate was applied to a silica gel column and the product eluted with ethyl acetate. The product fractions were concentrated to give a foam that solidified to a pink solid (105 mg, 80%).

$^1$H NMR (400 MHz, chloroform-d) δ ppm 3.18 (s, 1H) 3.29-3.39 (m, 10H) 3.49-3.57 (m, 4H) 4.09-4.19 (bd, 1H) 4.31-4.42 (m, 1H) 6.35 (bd, J=13.35 Hz, 1H) 7.41 (t, J=7.55 Hz, 2H) 7.47-7.54 (m, 2H) 7.56 (d, J=1.76 Hz, 1H) 7.60 (d, J=8.06 Hz, 3H) 7.81 (dd, J=8.31, 1.76 Hz, 1H) 8.01 (s, 1H).

LCMS (5-95% acetonitrile/water/10 mM ammonium acetate; 2 ml/min, 4 min gradient, Xbridge C18 4.6×50 mm 10 u, 254 nm) Rt=2.05 min, 100%, ES$^+$=429, 430.

HPLC (5-95% acetonitrile/water/10 mM ammonium acetate; 1 ml/min, 15 min gradient, Gemini C18 4.6×150 mm S5, 254 nm): Rt=13.36 min, 97.6%.

HPLC (5-95% acetonitrile/water/10 mM ammonium acetate; 1 ml/min, 15 min gradient, Xbridge C18 4.6×150 mm S3.5, 254 nm): Rt=12.68 min, 97.1%

Example 16

8-Ethynyl-N,N-bis(2-methoxyethyl)-6-phenyl-4H-benzo[f]imidazo[1,5-a][1,4]diazepine-3-carboxamide. This compound was prepared in a manner similar to Example 12 using 8-ethynyl-6-phenyl-4H-benzo[f]imidazo[1,5-a][1,4]diazepine-3-carbonyl fluoride (101 mg, 0.307 mmol) and bis(2-methoxyethyl)amine (136 μL, 0.921 mmol). The crude material was applied to a silica gel column and the product eluted with ethyl acetate/methanol. The product factions were concentrated, and dried at 80° C. under high vacuum to give a solid (90.5 mg, 66.6%).

$^1$H NMR (400 MHz, chloroform-D) δ ppm 3.23 (s, 1H) 3.28-3.36 (m, 6H) 3.66 (t, J=4.91 Hz, 4H), 3.72 (s, 2H) 3.93 (s, 2H) 7.24 (s, 1H) 7.50 (t, J=7.81 Hz, 2H) 7.63 (t, J=7.43 Hz, 1H) 7.74 (ddd, J=13.35, 8.56, 4.78 Hz, 3H) 7.91 (dd, J=8.44, 1.89 Hz, 1H).

MS: ES$^+$=442.62, 443.67.

HPLC (5-95% acetonitrile/water/10 mM ammonium acetate; 1 ml/min, 15 min gradient, Xbridge C18 4.6×150 mm S3.5, 254 nm): Rt=13.71 min, 96.3%

HPLC (5-95% acetonitrile/water/10 mM ammonium acetate; 1 ml/min, 15 min gradient, Gemini C18 4.6×150 mm S5, 254 nm): Rt=15.27 min, 98.1%.

Example 17

8-Ethynyl-N-(1-methoxypropan-2-yl)-6-phenyl-4H-benzo[f]imidazo[1,5-a][1,4]diazepine-3-carboxamide. This compound was prepared in a manner similar to Example 12 using 8-ethynyl-6-phenyl-4H-benzo[f]imidazo[1,5-a][1,4]diazepine-3-carbonyl fluoride (101 mg, 0.307 mmol) and 1-methoxypropan-2-amine (97 μL, 0.921 mmol). The crude material was applied to a silica gel column and the product eluted with ethyl acetate/methanol. The product factions were concentrated, and dried at 80° C. under high vacuum to give a solid (58.1 mg, 47.8%).

$^1$H NMR (400 MHz, chloroform-D) δ ppm 1.24 (s, 4H) 3.17 (s, 1H) 3.35 (s, 4H) 3.43 (td, J=9.19, 4.78 Hz, 2H) 4.11 (s, 1H) 4.30 (s, 1H) 7.24 (s, 1H) 7.37-7.49 (m, 4H) 7.55-7.64 (m, 4H) 7.80 (d, J=8.31 Hz, 1H) 8.10 (s, 1H).

MS: ES$^+$=398.66, 399.66.

HPLC (5-95% acetonitrile/water/10 mM ammonium acetate; 1 ml/min, 15 min gradient, Xbridge C18 4.6×150 mm S3.5, 254 nm): Rt=13.76 min, 98.5%

HPLC (5-95% acetonitrile/water/10 mM ammonium acetate; 1 ml/min, 15 min gradient, Gemini C18 4.6×150 mm S5, 254 nm): Rt=14.62 min, 99.9%.

Example 18

8-Ethynyl-N-(3-methoxypropyl)-6-phenyl-4H-benzo[f] imidazo[1,5-a][1,4]diazepine-3-carboxamide. This compound was prepared in a manner similar to Example 12 using 8-ethynyl-6-phenyl-4H-benzo[f]imidazo[1,5-a][1,4]diazepine-3-carbonyl fluoride (100 mg, 0.305 mmol) and 3-methoxypropan-1-amine (0.093 mL, 0.915 mmol). The crude material was applied to a silica gel column and the product eluted with ethyl acetate/methanol. The product factions were concentrated, and dried at 80° C. under high vacuum to give a solid (40.3 mg, 33%).

$^1$H NMR (400 MHz, chloroform-D) δ ppm 1.84 (dq, J=6.55, 6.38 Hz, 2H) 2.15 (s, 1 H) 3.17 (s, 1H) 3.32 (s, 3H) 3.41-3.51 (m, 4H) 4.05-4.16 (m, 1H) 7.39 (t, J=7.81 Hz, 2H) 7.43-7.51 (m, 1H) 7.54-7.59 (m, 3H) 7.64 (d, J=8.56 Hz, 2H) 7.80 (d, J=8.31 Hz, 1H).

MS: ES$^+$=398.64, 399.64.

HPLC (5-95% acetonitrile/water/10 mM ammonium acetate; 1 ml/min, 15 min gradient, Xbridge C18 4.6×150 mm S3.5, 254 nm): Rt=13.59 min, 99.8%

HPLC (5-95% acetonitrile/water/10 mM ammonium acetate; 1 ml/min, 15 min gradient, Gemini C18 4.6×150 mm S5, 254 nm): Rt=14.25 min, 100%.

Example 19

8-Ethynyl-6-phenyl-N-(2-propoxyethyl)-4H-benzo[f] imidazo[1,5-a][1,4]diazepine-3-carboxamide. This compound was prepared in a manner similar to Example 12 using 8-ethynyl-6-phenyl-4H-benzo[f]imidazo[1,5-a][1,4]diazepine-3-carbonyl fluoride (0.100 g, 0.305 mmol) and 2-propoxyethanamine (94 mg, 0.915 mmol). The crude material was applied to a silica gel column and the product eluted with ethyl acetate/methanol. The product factions were concentrated, and dried at 80° C. under high vacuum to give a solid (89.2 mg, 70%).

$^1$H NMR (400 MHz, chloroform-D) δ ppm 0.89 (t, J=7.43 Hz, 3H) 1.52-1.62 (m, J=7.43, 7.08, 7.08, 7.08, 7.08 Hz, 2H) 3.18 (s, 1H) 3.39 (t, J=6.67 Hz, 2H) 3.55 (d, J=3.53 Hz, 4H) 7.24 (s, 1H) 7.41 (t, J=7.55 Hz, 2H) 7.50 (t, J=7.43 Hz, 1H) 7.55-7.66 (m, 4H).

MS: ES$^+$=412.66, 413.66.

HPLC (5-95% acetonitrile/water/10 mM ammonium acetate; 1 ml/min, 15 min gradient, Xbridge C18 4.6×150 mm S3.5, 254 nm): Rt=14.51 min, 97.8%

HPLC (5-95% acetonitrile/water/10 mM ammonium acetate; 1 ml/min, 15 min gradient, Gemini C18 4.6×150 mm S5, 254 nm): Rt=15.30 min, 99.7%.

Example 20

8-Ethynyl-N-(2-isopropoxyethyl)-6-phenyl-4H-benzo[f] imidazo[1,5-a][1,4]diazepine-3-carboxamide. This compound was prepared in a manner similar to Example 12 using 8-ethynyl-6-phenyl-4H-benzo[f]imidazo[1,5-a][1,4]diazepine-3-carbonyl fluoride (129 mg, 0.392 mmol) and 2-isopropoxyethanamine (52.5 mg, 0.509 mmol). The crude material was applied to a silica gel column and the product eluted with ethyl acetate/methanol. The product factions were concentrated, and dried at 80° C. under high vacuum to give a solid (109.4 mg, 67.7%).

$^1$H NMR (400 MHz, chloroform-D) δ ppm 1.14 (d, J=6.04 Hz, 6H) 3.19 (s, 1H) 3.57 (td, J=11.96, 5.54 Hz, 5H) 7.24 (s, 1H) 7.42 (t, J=7.68 Hz, 2H) 7.52 (t, J=7.43 Hz, 1H) 7.64 (dd, J=11.83, 7.81 Hz, 3H).

MS: ES$^+$=412.65, 413.64.

HPLC (5-95% acetonitrile/water/10 mM ammonium acetate; 1 ml/min, 15 min gradient, Xbridge C18 4.6×150 mm S3.5, 254 nm): Rt=14.30 min, 98.2%

HPLC (5-95% acetonitrile/water/10 mM ammonium acetate; 1 ml/min, 15 min gradient, Gemini C18 4.6×150 mm S5, 220 nm): Rt=15.15 min, 96.8%.

Example 21

(8-Ethynyl-6-phenyl-4H-benzo[f]imidazo[1,5-a][1,4]diazepin-3-yl)(4-(pyrimidin-2-yl)piperazin-1-yl)methanone. This compound was prepared in a manner similar to Example 12 using 8-ethynyl-6-phenyl-4H-benzo[f]imidazo[1,5-a][1,4]diazepine-3-carbonyl fluoride (129 mg, 0.392 mmol), saturated Na2CO3 (2 ml), and 2-(piperazin-1-yl)pyrimidine dihydrochloride (101 mg, 0.426 mmol). The crude material was applied to a silica gel column and the product eluted with ethyl acetate/methanol. The product factions were concentrated, and dried at 80° C. under high vacuum to give a solid (127.6 mg, 68.8%).

$^1$H NMR (400 MHz, chloroform-D) δ ppm 3.13-3.20 (m, 1H) 3.80 (s, 1H) 3.88 (s, 1H) 4.09-4.21 (m, 5H) 5.90-6.01 (m, 1H) 7.24 (s, 1H) 7.44 (t, J=7.68 Hz, 2H) 7.52-7.63 (m, 4H) 7.78-7.88 (m, 1H) 7.90-7.97 (m, 1H) 8.47 (d, J=4.78 Hz, 1H).

MS: ES$^+$=473.64, 474.64.

HPLC (5-95% acetonitrile/water/10 mM ammonium acetate; 1 ml/min, 15 min gradient, Xbridge C18 4.6×150 mm S3.5, 254 nm): Rt=13.89 min, 96.5%

HPLC (5-95% acetonitrile/water/10 mM ammonium acetate; 1 ml/min, 15 min gradient, Gemini C18 4.6×150 mm S5, 220 nm): Rt=14.50 min, 99.0%.

Example 22

N,N'-(Pentane-1,5-diyl)bis(8-ethynyl-6-phenyl-4H-benzo [f]imidazo[1,5-a][1,4]diazepine-3-carboxamide). This compound was prepared in a manner similar to Example 12 using 8-ethynyl-6-phenyl-4H-benzo[f]imidazo[1,5-a][1,4]diazepine-3-carbonyl fluoride (129 mg, 0.392 mmol) and pentane-1,5-diamine (20.01 mg, 0.196 mmol). The crude material was applied to a silica gel column and the product eluted with ethyl acetate/methanol. The product factions were concentrated, and dried at 80° C. under high vacuum to give a solid (119.6 mg, 42.4%).

$^1$H NMR (400 MHz, chloroform-D) δ ppm 1.43 (dq, J=7.81, 7.64 Hz, 1H) 1.55-1.66 (m, J=7.18, 7.18, 7.05, 6.80 Hz, 2H) 3.16 (s, 1H) 3.38 (s, 2H) 4.02-4.14 (m, 1H) 6.25 (d, J=11.33 Hz, 1H) 7.37 (t, J=7.43 Hz, 2H) 7.41-7.48 (m, 1H) 7.48-7.58 (m, 4H) 7.71-7.82 (m, 2H).

MS: ES$^+$: 720.63, 721.65, 722.62.

HPLC (5-95% acetonitrile/water/10 mM ammonium acetate; 1 ml/min, 15 min gradient, Xbridge C18 4.6×150 mm S3.5, 254 nm): Rt=14.27 min, 94.0%

HPLC (5-95% acetonitrile/water/10 mM ammonium acetate; 1 ml/min, 15 min gradient, Gemini C18 4.6×150 mm S3.5, 254 nm): Rt=15.02 min, 97.8%.

Example 23

N,N'-(2,2'-Oxybis(ethane-2,1-diyl))bis(8-ethynyl-6-phenyl-4H-benzo[f]imidazo[1,5-a][1,4]diazepine-3-carboxamide). This compound was prepared in a manner similar to Example 12 using 8-ethynyl-6-phenyl-4H-benzo[f]imidazo[1,5-a][1,4]diazepine-3-carbonyl fluoride (129 mg, 0.392 mmol) and 2,2'-oxydiethanamine (20.40 mg, 0.196 mmol). The crude material was applied to a silica gel column and the product eluted with ethyl acetate/methanol. The product factions were concentrated, and dried at 80° C. under high vacuum to give a solid (121.8 mg, 43%).

$^1$H NMR (400 MHz, chloroform-D) δ ppm 1.23 (s, 2H) 2.01 (s, 2H) 3.17 (s, 1H) 3.58 (s, 2H) 3.61 (d, J=4.53 Hz, 3H) 4.07 (d, J=10.07 Hz, 2H) 6.24 (d, J=10.83 Hz, 1H) 7.37 (t, J=7.43 Hz, 2H) 7.41-7.49 (m, 1H) 7.49-7.56 (m, 4H) 7.82 (dd, J=8.44, 1.64 Hz, 1H) 7.96 (s, 1H) 8.07 (s, 1H).

MS: ES$^+$=722.62, 723.62.

HPLC (5-95% acetonitrile/water/10 mM ammonium acetate; 1 ml/min, 15 min gradient, Xbridge C18 4.6×150 mm S3.5, 254 nm): Rt=14.14 min, 95.6%

HPLC (5-95% acetonitrile/water/10 mM ammonium acetate; 1 ml/min, 15 min gradient, Gemini C18 4.6×150 mm S5, 254 nm): Rt=14.65 min, 98.0%.

Example 24

N,N'-(2,2'-(Methylazanediyl)bis(ethane-2,1-diyl))bis(8-ethynyl-6-phenyl-4H-benzo[f]imidazo[1,5-a][1,4]diazepine-3-carboxamide). This compound was prepared in a manner similar to Example 12 using 8-ethynyl-6-phenyl-4H-benzo[f]imidazo[1,5-a][1,4]diazepine-3-carbonyl fluoride (129 mg, 0.392 mmol) and N1-(2-aminoethyl)-N1-methylethane-1,2-diamine (22.95 mg, 0.196 mmol). The crude material was applied to a silica gel column and the product eluted with ethyl acetate/methanol. The product factions were concentrated, and dried at 80° C. under high vacuum to give a solid (93.6 mg, 32.5%).

$^1$H NMR (400 MHz, chloroform-D) δ ppm 2.68 (s, 1H) 3.05 (s, 1H) 3.13 (s, 1H) 3.73 (s, 1H) 3.99 (d, J=12.34 Hz, 1H) 6.12 (d, J=11.08 Hz, 1H) 7.32 (t, J=7.43 Hz, 2H) 7.40 (t, J=7.30 Hz, 1H) 7.45 (d, J=7.05 Hz, 2H) 7.48-7.52 (m, 2H) 7.70 (dd, J=8.31, 1.76 Hz, 1H) 7.82-7.93 (m, 2H).

MS: ES$^+$=735.65, 736.68, 737.68.

HPLC (5-95% acetonitrile/water/10 mM ammonium acetate; 1 ml/min, 15 min gradient, Xbridge C18 4.6×150 mm S3.5, 254 nm): Rt=14.47 min, 91.8%

HPLC (5-95% acetonitrile/water/10 mM ammonium acetate; 1 ml/min, 15 min gradient, Gemini C18 4.6×150 mm S5, 254 nm): Rt=14.29 min, 99.3%

Example 25

N,N'-(2,2'-Thiobis(ethane-2,1-diyl))bis(8-ethynyl-6-phenyl-4H-benzo[f]imidazo[1,5-a][1,4]diazepine-3-carboxamide). This compound was prepared in a manner similar to Example 12 using 8-ethynyl-6-phenyl-4H-benzo[f]imidazo[1,5-a][1,4]diazepine-3-carbonyl fluoride (129 mg, 0.392 mmol) and 2,2'-thiodiethanamine (23.54 mg, 0.196 mmol). The crude material was applied to a silica gel column and the product eluted with ethyl acetate/methanol. The product factions were concentrated, and dried at 80° C. under high vacuum to give a solid (60.4 mg, 20.9%).

$^1$H NMR (400 MHz, chloroform-D) δ ppm 2.68-2.79 (m, 2H) 3.19 (s, 1H) 3.50 (s, 2H) 4.26 (s, 1H) 6.26 (d, J=10.32 Hz, 1H) 7.43 (t, J=7.68 Hz, 3H) 7.49-7.59 (m, 3H) 7.60-7.71 (m, 3H) 7.91 (t, J=8.81 Hz, 1H) 8.10 (s, 1H) 8.17 (s, 1H).

MS: ES$^+$=738.59, 739.58, 740.57.

HPLC (5-95% acetonitrile/water/10 mM ammonium acetate; 1 ml/min, 15 min gradient, Xbridge C18 4.6×150 mm S3.5, 254 nm): Rt=14.72 min, 93.6%

HPLC (5-95% acetonitrile/water/10 mM ammonium acetate; 1 ml/min, 15 min gradient, Gemini C18 4.6×150 mm S5, 254 nm): Rt=15.32 min, 97.4%.

Example 26

8-Ethynyl-N-(2-hydroxybutyl)-6-phenyl-4H-benzo[f]imidazo[1,5-a][1,4]diazepine-3-carboxamide. This compound was prepared from 8-ethynyl-6-phenyl-4H-benzo[f]imidazo[1,5-a][1,4]diazepine-3-carboxylic acid (333 mg, 0.101 mmol), carbonyl diimidazole (198 mg, 1.22 mmol), and 1-aminobutan-2-ol (0.202 mL, 2.14 mmol) in THF (10 mL) via the method shown in Example 4, Method 3. The solution was diluted with ethyl acetate, extracted with water, and dried with brine. The organic layer was concentrated and the residue dissolved in THF (25 ml). The solution was filtered and 4N HCl in dioxane (0.75 ml, 3 mmole) was added to give a white precipitate. The precipitate were filtered, washed with ethyl acetate and then dried at 80° C. under high vacuum for 2 hr to give a white powder (259.6 mg, 63%).

$^1$H NMR (400 MHz, DMSO-D6) δ ppm 0.87 (t, J=7.43 Hz, 3H) 1.26-1.36 (m, 1H) 1.36-1.47 (m, 1H) 3.45-3.55 (m, 1H) 4.41 (s, 1H) 5.94 (s, 2H) 7.40 (d, J=1.26 Hz, 1H) 7.45-7.52 (m, 4H) 7.53-7.59 (m, 1H) 7.69 (d, J=1.26 Hz, 2H) 7.89-7.99 (m, 3H) 8.46 (s, 1H) 14.62 (s, 1H).

LCMS (5-95% acetonitrile/water/10 mM ammonium acetate; 4 ml/min, 4 min gradient, Phenomenex Luna C18 4.6×50 mm 10 u, 254 nm) Rt=2.12 min, 100%, ES$^+$=399, 420.

HPLC (5-95% acetonitrile/water/10 mM ammonium acetate; 1 ml/min, 15 min gradient, Xterra C18 4.6×150 mm S3.5, 254 nm): Rt=10.27 min, 96.7%

HPLC (5-95% acetonitrile/water/10 mM ammonium acetate; 1 ml/min, 15 min gradient, Xbridge C18 4.6×150 mm S3.5, 254 nm): Rt=9.93 min, 96.6%.

Example 27

8-Ethynyl-N—((R)-2-hydroxypropyl)-6-phenyl-4H-benzo[f]imidazo[1,5-a][1,4]diazepine-3-carboxamide. This compound was prepared from 8-ethynyl-6-phenyl-4H-benzo[f]imidazo[1,5-a][1,4]diazepine-3-carboxylic acid (333 mg, 0.101 mmol), carbonyl diimidazole (198 mg, 1.22 mmol), and (R)-1-aminopropan-2-ol (0.165 mL, 2.138 mmol) in THF (10 mL) via the method shown in Example 4, Method 3. The solution was diluted with ethyl acetate, extracted with water, and dried with brine. The organic layer was concentrated and the residue dissolved in THF (25 ml). The solution was filtered and 4N HCl in dioxane (0.75 ml, 3 mmole) was added to give a white precipitate. The precipitate were filtered, washed with ethyl acetate and then dried at 80° C. under high vacuum for 2 hr to give a white powder (388 mg, 99%).

$^1$H NMR (400 MHz, DMSO-D6) δ ppm 1.04 (d, J=6.04 Hz, 3H) 3.11-3.20 (m, 1H) 3.29 (ddd, J=12.46, 6.17, 6.04 Hz, 1H) 3.72-3.80 (m, 1H) 4.42 (s, 1H) 7.40 (d, J=1.51 Hz, 1H) 7.45-7.54 (m, 4H) 7.56-7.61 (m, 1H) 7.68 (d, J=1.26 Hz, 2H) 7.93-8.03 (m, 3H) 8.49 (s, 1H) 9.13 (s, 1H) 14.69 (s, 1H).

LCMS (5-95% acetonitrile/water/10 mM ammonium acetate; 4 ml/min, 4 min gradient, Phenomenex Luna C18 4.6×50 mm 10 u, 254 nm) Rt=1.96 min, 100%, ES$^+$=385, ES$^-$=383.

HPLC (5-95% acetonitrile/water/10 mM ammonium acetate; 1 ml/min, 15 min gradient, Xterra C18 4.6×150 mm S3.5, 254 nm): Rt=9.58 min, 96.2%

HPLC (5-95% acetonitrile/water/10 mM ammonium acetate; 1 ml/min, 15 min gradient, Xbridge C18 4.6×150 mm S3.5, 254 nm): Rt=9.29 min, 96.0%.

Example 28

8-Ethynyl-N—((S)-2-hydroxypropyl)-6-phenyl-4H-benzo[f]imidazo[1,5-a][1,4]diazepine-3-carboxamide. This compound was prepared from 8-ethynyl-6-phenyl-4H-benzo[f]imidazo[1,5-a][1,4]diazepine-3-carboxylic acid (333 mg, 0.101 mmol), carbonyl diimidazole (198 mg, 1.22 mmol), and (S)-1-aminopropan-2-ol (0.165 mL, 2.138 mmol) in THF (10 mL) via the method shown in Example 4, Method 3. The solution was diluted with ethyl acetate, extracted with water, and dried with brine. The organic layer was concentrated and the residue dissolved in THF (25 ml). The solution was filtered and 4N HCl in dioxane (0.75 ml, 3 mmole) was added to give a white precipitate. The precipitate were filtered, washed with ethyl acetate and then dried at 80° C. under high vacuum for 2 hr to give a white powder (358 mg, 91.5%).

$^1$H NMR (400 MHz, DMSO-D6) δ ppm 1.05 (d, J=6.30 Hz, 3H) 3.11-3.20 (m, 1H) 3.29 (ddd, J=12.46, 6.17, 6.04 Hz, 1H) 3.72-3.80 (m, 1H) 4.42 (s, 1H) 6.84 (none, 1H) 7.40 (d, J=1.01 Hz, 1H) 7.46-7.54 (m, 4H) 7.55-7.63 (m, 1H) 7.69 (d, J=1.26 Hz, 1H) 7.94-8.03 (m, 3H) 8.48 (s, 1H).

LCMS (5-95% acetonitrile/water/10 mM ammonium acetate; 4 ml/min, 6 min gradient, Phenomenex Luna C18 4.6×50 mm 10 u, 254 nm) Rt=1.96 min, 100%, ES$^+$=385, ES$^-$=383.

HPLC (5-95% acetonitrile/water/10 mM ammonium acetate; 1 ml/min, 15 min gradient, Xterra C18 4.6×150 mm S3.5, 254 nm): Rt=9.58 min, 95.6%

HPLC (5-95% acetonitrile/water/10 mM ammonium acetate; 1 ml/min, 15 min gradient, Xbridge C18 4.6×150 mm S3.5, 254 nm): Rt=9.28 min, 95.3%.

Example 29

8-Ethynyl-N-(3-hydroxypropyl)-6-phenyl-4H-benzo[f]imidazo[1,5-a][1,4]diazepine-3-carboxamide dihydrochloride. This compound was prepared from 8-ethynyl-6-phenyl-4H-benzo[f]imidazo[1,5-a][1,4]diazepine-3-carboxylic acid (253 mg, 0.773 mmol), carbonyl diimidazole (138 mg, 0.85 mmol), and 3-aminopropan-1-ol (0.116 g, 1.547 mmol) in NMP (5 mL) via the method shown in Example 4, Method 3. The solution was diluted with ethyl acetate, extracted with water, and dried with brine. The organic layer was concentrated and the residue dissolved in ethyl acetate (25 ml). The solution was filtered and 4N HCl in dioxane (1 ml, 4 mmole) was added to give a white precipitate. The precipitate were filtered, washed with ethyl acetate and then dried at 80° C. under high vacuum for 2 hr to give a white powder (275 mg, 77.8%).

$^1$H NMR (400 MHz, DMSO-d$_6$) δ ppm 1.64 (d, J=6.30 Hz, 1H) 3.32 (d, J=6.30 Hz, 2H) 3.45 (t, J=6.17 Hz, 2H) 4.45 (s, 1H) 7.41 (br. s., 1H) 7.46-7.57 (m, 5H) 7.62 (d, J=6.04 Hz, 1H) 8.00 (s, 2H) 8.29 (t, J=5.54 Hz, 1H) 8.51 (s, 1H)

LCMS (5-95% acetonitrile/water/10 mM ammonium acetate; 4 ml/min, 6 min gradient, Phenomenex Luna C18 4.6×50 mm 10 u, 254 nm) Rt=2.48 min, 100%, ES$^+$=385, ES$^-$=383.

HPLC (5-95% acetonitrile/water/10 mM ammonium acetate; 1 ml/min, 15 min gradient, Xbridge C18 4.6×150 mm S3.5, 254 nm): Rt=9.85 min, 95.6%.

Example 30

8-Ethynyl-N-(5-hydroxypentyl)-6-phenyl-4H-benzo[f]imidazo[1,5-a][1,4]diazepine-3-carboxamide dihydrochloride. This compound was prepared from 8-ethynyl-6-phenyl-4H-benzo[f]imidazo[1,5-a][1,4]diazepine-3-carboxylic acid (253 mg, 0.773 mmol), carbonyl diimidazole (138 mg, 0.85 mmol), and 5-aminopentan-1-ol (0.160 g, 1.547 mmol) in NMP (5 mL) via the method shown in Example 4, Method 3. The solution was diluted with ethyl acetate, extracted with water, and dried with brine. The organic layer was concentrated and the residue dissolved in ethyl acetate (25 ml). The solution was filtered and 4N HCl in dioxane (1 ml, 4 mmole) was added to give a white precipitate. The precipitate were filtered, washed with ethyl acetate and then dried at 80° C. under high vacuum for 2 hr to give a white powder (375 mg, 99.9%).

$^1$H NMR (400 MHz, DMSO-d6) δ ppm 1.24-1.36 (m, 2H) 1.37-1.44 (m, 2H) 1.44-1.56 (m, 2H) 1.84-1.94 (m, 1H) 2.17 (t, J=8.06 Hz, 1H) 2.69 (s, 2H) 3.24 (q, J=6.55 Hz, 2H) 3.27-3.33 (m, 1H) 3.36 (t, J=6.42 Hz, 2H) 4.48 (s, 1H) 7.41 (s, 1H) 7.51-7.63 (m, 4H) 7.70 (t, J=6.29 Hz, 1H) 7.99-8.11 (m, 2H) 8.36 (t, J=6.04 Hz, 1H) 8.63 (s, 1H).

LCMS (5-95% acetonitrile/water/10 mM ammonium acetate; 4 ml/min, 6 min gradient, Phenomenex Luna C18 4.6×50 mm 10 u, 254 nm) Rt=2.69 min, 100%, ES$^+$=413, ES$^-$=411.

HPLC (5-95% acetonitrile/water/10 mM ammonium acetate; 1 ml/min, 15 min gradient, Xbridge phenyl 4.6×150 mm S3.5, 254 nm): Rt=10.65 min, 95.2%.

Example 31

8-Ethynyl-N-(4-hydroxybutyl)-6-phenyl-4H-benzo[f]imidazo[1,5-a][1,4]diazepine-3-carboxamide dihydrochloride. This compound was prepared in a manner similar to Example 12 using 8-ethynyl-6-phenyl-4H-benzo[f]imidazo[1,5-a][1,4]diazepine-3-carbonyl fluoride (329 mg, 1 mmol) and 4-aminobutan-1-ol (0.184 mL, 2 mmol). The crude product was dissolved in methylene chloride and applied to a silica gel. The product was eluted with step gradient of 100% ethyl acetate to 30% methanol/ethyl acetate and the product fractions were concentrated to a foamy solid. The solid was dissolved in ethyl acetate and 4N HCl in dioxane (0.6 ml, 2.4 mmol) was added to give a white precipitate. The precipitate was filtered, washed with ethyl acetate, and air dried. The material was dried under low vac at room temperature overnight to give a white powder (272 mg, 57.7%).

$^1$H NMR (400 MHz, DMSO-d6) δ ppm 1.36-1.47 (m, 2H) 1.47-1.59 (m, 2H) 3.25 (q, J=6.30 Hz, 2H) 3.39 (t, J=6.42 Hz, 2H) 4.45 (s, 1H) 7.41 (s, 1H) 7.48-7.58 (m, 4H) 7.64 (t, J=6.67 Hz, 1H) 8.01 (s, 2H) 8.28 (t, J=5.92 Hz, 2H) 8.53 (s, 1H)

LCMS (5-95% acetonitrile/water/10 mM ammonium acetate; 4 ml/min, 4 min gradient, Phenomenex Luna C18 4.6×50 mm 10 u, 220 nm) Rt=1.79 min, 98.8%, ES$^-$=397, ES$^+$=399.

HPLC (5-95% acetonitrile/water/10 mM ammonium acetate; 1 ml/min, 15 min gradient, Xbridge C18 4.6×150 mm S3.5, 254 nm): Rt=10.33 min, 99.4%

HPLC (5-95% acetonitrile/water/10 mM ammonium acetate; 1 ml/min, 15 min gradient, Xbridge phenyl 4.6×150 mm S3.5, 254 nm): Rt=10.56 min, 99.49%.

Example 32

2-(8-Ethynyl-6-phenyl-4H-benzo[f]imidazo[1,5-a][1,4]diazepine-3-carboxamido)ethyl acetate dihydrochloride. A mixture of 8-ethynyl-N-(2-hydroxyethyl)-6-phenyl-4H-benzo[f]imidazo[1,5-a][1,4]diazepine-3-carboxamide (2.25 g, 6.07 mmol), acetic anhydride (4.5 mL, 47.7 mmol), and triethylamine (4.5 mL, 32.3 mmol) in NMP (10 mL) was heated in a hot water bath for 1 hr. The solution was poured into water, and the mixture extracted with ethyl acetate. The ethyl acetate layer was extracted with water, dried with brine, and concentrated. The crude product was purified on silica gel column using ethyl acetate as the eluent. The product fractions were concentrated to give a white solid (2.22 g, 89%). The solid was dissolved in ethyl acetate and 4N HCl in dioxane (3 ml, 12 mmole) was added drop-wise from a syringe. The white precipitate was filtered, washed with ethyl acetate and air dried. The white powder was dried under low vac for 1 hr (2.131 g, 72.3%).

$^1$H NMR (400 MHz, DMSO-d6) d ppm 1.99 (s, 4H) 3.49 (q, J=5.79 Hz, 2H) 4.11 (t, J=5.79 Hz, 2H) 4.38-4.49 (m, 2H) 5.94 (br. s., 1H) 7.41 (s, 1H) 7.49-7.60 (m, 5H) 7.65 (t, J=6.92 Hz, 1H) 8.02 (s, 2H) 8.42 (t, J=6.04 Hz, 1H) 8.54 (s, 1H).

LCMS (5-95% acetonitrile/water/10 mM ammonium acetate; 4 ml/min, 6 min gradient, Phenomenex Luna C18 4.6×50 mm 10 u, 254 nm) Rt=2.85 min, 99.2%, ES$^+$=413.

HPLC (5-95% acetonitrile/water/10 mM ammonium acetate; 1 ml/min, 15 min gradient, Xbridge C18 4.6×150 mm S3.5, 254 nm): Rt=11.73 min, 94.5%

HPLC (5-95% acetonitrile/water/10 mM ammonium acetate; 1 ml/min, 15 min gradient, Xbridge phenyl 4.6×150 mm S3.5, 254 nm): Rt=11.83 min, 99.2%.

Example 33

2-(8-Ethynyl-6-phenyl-4H-benzo[f]imidazo[1,5-a][1,4] diazepine-3-carboxamido)acetic acid. A mixture of ethyl 2-(8-ethynyl-6-phenyl-4H-benzo[f]imidazo[1,5-a][1,4]diazepine-3-carboxamido)acetate (1.08 g, 2.62 mmol) and lithium hydroxide hydrate (0.354 g, 8.44 mmol) in THF (10 mL) and water (10.00 mL) was stirred for 1 hr at room temperature. An additional amount of water (10.00 mL) was added to give a clear solution. The solution was concentrated to remove the THF. The aqueous solution was made slightly acidic with 1N HCl to give a white precipitate which was filtered, washed with water, and air dried. The white powder was dried in vacuo at 60° C. for 2 hr to give a white powder (0.77 g, 75%).

$^1$H NMR (400 MHz, DMSO-d$_6$) δ ppm 3.90 (d, J=6.04 Hz, 2H) 4.08 (d, J=12.34 Hz, 1H) 4.38 (s, 1H) 5.91 (d, J=12.59 Hz, 1H) 7.38-7.51 (m, 7H), 7.84-7.96 (m, 2H) 8.31 (t, J=6.04 Hz, 1H) 8.41 (s, 1H).

LCMS (5-95% acetonitrile/water/10 mM ammonium acetate; 4 ml/min, 6 min gradient, Phenomenex Luna C18 4.6×50 mm 10 u, 254 nm) Rt=1.83 min, 100%, ES$^+$=385, ES$^-$=383.

HPLC (5-95% acetonitrile/water/10 mM ammonium acetate; 1 ml/min, 15 min gradient, Xbridge C18 4.6×150 mm S3.5, 254 nm): Rt=9.51 min, 98.9%

HPLC (5-95% acetonitrile/water/10 mM ammonium acetate; 1 ml/min, 15 min gradient, Xbridge phenyl 4.6×150 mm S3.5, 254 nm): Rt=11.75 min, 98.0%.

Example 34

Step 1

2-Bromo-N-(4-bromo-2-(2-fluorobenzoyl)phenyl)acetamide. A mixture of (2-amino-5-bromophenyl)(2-fluorophenyl)methanone (15 g, 51.0 mmol) and sodium bicarbonate (12.85 g, 153 mmol) in CHCl$_3$ (150 mL) was cooled in an ice bath to 0° C. A solution of 2-bromoacetyl bromide (4.89 mL, 56.1 mmol) was added drop-wise slowly and washed in with CHCl$_3$ (30 ml). The cooling was removed and the mixture was stirred for 2 hr.

The reaction mixture was washed with aqueous NaHCO3 (5%) and dried with brine. The CHCl$_3$ was removed in vacuo and the residue was stirred with. The solid product was filtered, washed with ether and air dried to a yellow powder. The material was taken on without purification.

Step 2

7-Bromo-5-(2-fluorophenyl)-1H-benzo[e][1,4]diazepin-2 (3H)-one. The product from Step 1 (21.17 g, 51 mmol) was dissolved in ammonia, 2M in methanol (400 mL, 800 mmol) that was further saturated with anhydrous ammonia. The solution was heated to reflux for 16 hr overnight, and allowed to cool to room temperature. The solution was concentrated and the residue was dissolved in ethyl acetate and water. The ethyl acetate layer was washed twice with water, dried with brine, and concentrated to give a yellow solid. The solid was recrystallized from ethyl acetate/hexane to give a white powder that was washed with hexane and air dried (9.65 g, 56.8%).

Step 3

8-Bromo-6-(2-fluorophenyl)-4H-benzo[f]imidazo[1,5-a] [1,4]diazepine-3-carboxylic acid. A solution of 7-bromo-5-(2-fluorophenyl)-1H-benzo[e][1,4]diazepin-2(3H)-one (3332 mg, 10 mmol) in THF (30 mL) was cooled in an ice bath as 60% sodium hydride in mineral oil (480 mg, 12.00 mmol) was added. After stirring for 20 min, diethyl phosphorochloridate (1.194 mL, 15.00 mmol) was added drop-wise and the yellow mixture was stirred for 30 min with ice bath cooling.

A solution of ethyl 2-isocyanoacetate (1.311 mL, 12.00 mmol) in THF (20 mL) was stirred with ice bath cooling as 60% sodium hydride in mineral oil (560 mg, 14.00 mmol) was added. After stirring for 15 min, this yellow mixture was added slowly to the cooled benzodiazepine reaction mixture. The combined mixture was stirred for 30 min with cooling, and then allowed to warm to room temperature 16 hr overnight.

The reaction was quenched with acetic acid and then poured into ice water. The product was extracted with ethyl acetate. The ethyl acetate extract was washed with water, dried with brine, and concentrated. The crude residue was purified on silica gel column using 60% ethyl acetate/methylene chloride as the eluent. The product fractions were concentrated to give a mixture of starting material and product as yellow resin that solidified. This material was stirred with lithium hydroxide hydrate (0.42 g, 10 mmol) in methanol (20 ml) and water (5 ml) for 60 hr at room temperature.

The mixture was concentrated and diluted with water and 1N NaOH (11 ml, 11 mmole) was added. The mixture was extracted with ethyl acetate and the aqueous layer was separated and made acidic with 1N HCl (22 ml, 22 mmole). The mixture was stirred for 10 min to give a pale yellow precipitate. The precipitate was filtered, washed with water, and air dried to give a pale yellow powder (843 mg, 20.85%).

$^1$H NMR (400 MHz, DMSO-d6) δ ppm 4.17 (1H, bs) 5.82 (1H, bs) 7.16-7.27 (m, 1H) 7.33 (t, J=7.55 Hz, 1H) 7.42 (d, J=2.27 Hz, 1H) 7.51-7.63 (m, 2H) 7.87 (d, J=8.81 Hz, 1H) 7.99 (dd, J=8.56, 2.27 Hz, 1H) 8.43 (s, 1H) 12.73 (1H, bs).

Step 4

8-Bromo-6-(2-fluorophenyl)-N-(2-methoxyethyl)-4H-benzo[f]imidazo[1,5-a][1,4]diazepine-3-carboxamide dihydrochloride. This compound was prepared from 8-bromo-6-(2-fluorophenyl)-4H-benzo[f]imidazo[1,5-a][1,4]diazepine-3-carboxylic acid (830 mg, 2.074 mmol), carbonyl diimidazole (404 mg, 2.489 mmol), and 2-methoxyethanamine (0.361 mL, 4.15 mmol) in NMP (10 mL) via the method shown in Example 4, Method 3. The yellow crude product was purified on silica gel using 0-20% methanol/ethyl acetate as the eluent. The product fractions were concentrated to give the free base as a pale yellow resin (0.60 g, 63%).

$^1$H NMR (400 MHz, chloroform-d) δ ppm 3.28 (s, 3H) 3.41-3.48 (br.t., 2H) 3.53 (br. t., 2H) 4.00 (br.s., 1H) 6.21 (br.s., 1H) 7.15 (t, J=8.06 Hz, 1H) 7.32-7.45 (m, 4H) 7.59 (td, J=7.62, 1.89 Hz, 1H) 7.67 (dd, J=8.56, 2.27 Hz, 1H) 7.82 (s, 1H).

This material was stirred in ethyl acetate as 4M HCl in dioxane (2 mL, 8.00 mmol) was added by syringe to give the di-HCl salt. The mixture was stirred for 5 min and the precipitate was filtered and air dried to a white powder (573 mg, 49.5%).

Step 5

8-Ethynyl-6-(2-fluorophenyl)-N-(2-methoxyethyl)-4H-benzo[f]imidazo[1,5-a][1,4]diazepine-3-carboxamide dihydrochloride. A mixture of 8-bromo-6-(2-fluorophenyl)-N-(2-methoxyethyl)-4H-benzo[f]imidazo[1,5-a][1,4]diazepine-3-carboxamide dihydrochloride (500 mg, 0.943 mmol), from Step 4, in acetonitrile (7 mL) and triethyl amine (10 mL) was degassed and heated to reflux under nitrogen. Bis(triphenylphosphine)palladium(II) acetate (35.3 mg, 0.047 mmol) was then quickly added, followed by the addition of TMS-acetylene (0.261 mL, 1.886 mmol). The mixture was stirred at reflux for 1 hr. The mixture was then concentrated, and diluted with saturated aqueous Na2CO3 and ethyl acetate. The mixture was filtered through celite, and the filtrate was extracted with ethyl acetate. The organic layer was dried with brine, and concentrated. The residue was purified on silica gel, eluting the product with ethyl acetate. The product fractions were concentrated. This material was dissolved in 1M tetrabutylammonium fluoride in THF (10 mL, 10.00 mmol) and stirred for 15 min. Water (1 ml) was added and the mixture was stirred for 15 min. The solution was concentrated and the residue was purified on silica gel using ethyl acetate as the eluent. The product fractions were concentrated. The product was dissolved in ethyl acetate and 4M HCl in dioxane (1 ml) was added to give a white precipitate that was filtered and air dried to give a white powder (183 mg, 41%).

$^1$H NMR (400 MHz, DMSO-d6) δ ppm 3.25 (s, 3H) 3.43 (b s, 5H) 4.18 (b s, 1H) 4.38 (s, 1H) 5.96 (b s, 1H) 7.22 (dd, J=10.45, 8.44 Hz, 1H) 7.28-7.38 (m, 2H) 7.52-7.64 (m, 2H) 7.82-7.89 (m, 1H) 7.89-7.97 (m, 1H) 8.08 (t, J=5.16 Hz, 1H) 8.48 (s, 1H), 10.17 (b s, 2H).

LCMS (5-95% acetonitrile/water/10 mM ammonium acetate; 4 ml/min, 6 min gradient, Phenomenex Luna C18 4.6×50 mm 10 u, 254 nm) Rt=2.76 min, 100%, ES$^+$=403.

HPLC (5-95% acetonitrile/water/10 mM ammonium acetate; 1 ml/min, 15 min gradient, Xbridge C18 4.6×150 mm S3.5, 254 nm): Rt=11.72 min, 100%.

HPLC (5-95% acetonitrile/water/10 mM ammonium acetate; 1 ml/min, 15 min gradient, Xbridge phenyl 4.6×150 mm S3.5, 254 nm): Rt=11.75 min, 99.4%.

Example 35

8-Ethynyl-N-(furan-2-ylmethyl)-6-phenyl-4H-benzo[f]imidazo[1,5-a][1,4]diazepine-3-carboxamide, dihydrochloride. This compound was prepared from 8-ethynyl-6-phenyl-4H-benzo[f]imidazo[1,5-a][1,4]diazepine-3-carboxylic acid, carbonyl diimidazole (150 mg, 0.927 mmol), and furfuryl amine (0.085 mL, 0.966 mmol) in dioxane (10 mL) via the method shown in Example 4, Method 3. The crude product was purified on silica gel using 50% ethyl acetate/methylene chloride as the eluent. The product fractions were concentrated to give a foamy solid that was dissolved in ethyl acetate (25 ml). 4M HCl in dioxane (1 mL, 4.0 mmol) was added to the stirred solution to give a white precipitate. The precipitate was filtered and air dried to a white powder (182 mg, 48.6%).

$^1$H NMR (400 MHz, DMSO-d6) δ ppm 4.36-4.48 (m, 4H) 6.21 (d, J=3.02 Hz, 1H) 6.33-6.42 (m, 1H) 7.41 (s, 1H) 7.47-7.58 (m, 5H) 7.63 (t, J=6.67 Hz, 1H) 8.01 (s, 2H) 8.52 (s, 1H) 8.67 (t, J=5.79 Hz, 1H).

LCMS (5-95% acetonitrile/water/10 mM ammonium acetate; 4 ml/min, 4 min gradient, Xbridge C18 4.6×50 mm 5 u, 254 nm) Rt=2.30 min, 100%, ES$^+$=407.

HPLC (5-95% acetonitrile/water/10 mM ammonium acetate; 1 ml/min, 15 min gradient, Xbridge C18 4.6×150 mm S3.5, 254 nm): Rt=11.40 min, 100%.

Example 36

8-Ethynyl-6-phenyl-N-((tetrahydrofuran-2-yl)methyl)-4H-benzo[f]imidazo[1,5-a][1,4]diazepine-3-carboxamide, dihydrochloride. This compound was prepared from 8-ethynyl-6-phenyl-4H-benzo[f]imidazo[1,5-a][1,4]diazepine-3-carboxylic acid (0.255 g, 0.779 mmol), carbonyl diimidazole (0.152 g, 0.935 mmol), and (tetrahydrofuran-2-yl)methanamine (0.101 mL, 0.974 mmol) in dioxane (10 mL) via the method shown in Example 4, Method 3. The crude product was purified on silica gel using 50% ethyl acetate/methylene chloride as the eluent. The product fractions were concentrated to a solid which was dissolved in ethyl acetate. 4M HCl in dioxane (1 mL, 4.0 mmol) was added to give a white precipitate. The mixture was concentrated and the white powder was washed with acetone and air dried (197 mg, 47.5%).

$^1$H NMR (400 MHz, DMSO-d6) δ ppm 1.53-1.64 (m, 1H) 1.77-1.89 (m, 3H) 3.32 (t, J=5.92 Hz, 2H) 3.61 (q, J=7.39 Hz, 1H) 3.70-3.82 (m, 1H) 3.97 (quin, J=6.17 Hz, 1H) 4.38-4.49 (m, 2H) 7.41 (s, 1H) 7.52-7.60 (m, 4H) 7.65 (t, J=6.92 Hz, 1H) 8.02 (s, 2H) 8.12 (t, J=6.04 Hz, 1H) 8.54 (s, 1H).

LCMS (5-95% acetonitrile/water/10 mM ammonium acetate; 4 ml/min, 4 min gradient, Xbridge C18 4.6×50 mm 5 u, 254 nm) Rt=2.08 min, 100%, ES$^+$=411.

HPLC (5-95% acetonitrile/water/10 mM ammonium acetate; 1 ml/min, 15 min gradient, Xbridge C18 4.6×150 mm S3.5, 254 nm): Rt=10.37 min, 100%.

HPLC (5-95% acetonitrile/water/10 mM ammonium acetate; 1 ml/min, 15 min gradient, Xbridge Phenyl 4.6×150 mm S3.5, 254 nm): Rt=10.45 min, 99.7%.

Example 37

8-Ethynyl-N-(2-methoxyethyl)-6-(pyridin-2-yl)-4H-benzo[f]imidazo[1,5-a][1,4]diazepine-3-carboxamide. A mixture of ethyl 8-ethynyl-6-(pyridin-2-yl)-4H-benzo[f]imidazo[1,5-a][1,4]diazepine-3-carboxylate (40 mg, 0.112 mmol) and lithium hydroxide (10 mg, 0.418 mmol) in water (1 mL) and THF (1 mL) was stirred for 18 hr overnight at room temp to give a clear solution. The THF was removed in a nitrogen stream, and 1N HCl (0.418 mL, 0.418 mmol) was added to give a white precipitate. The precipitate was filtered and air dried to give the carboxylic acid as a white powder (13.1 mg, 35.5%). The powder was heated with carbonyl diimidazole (10 mg, 0.062 mmol) in THF (1 mL) for 1 hr to give a clear solution. By syringe, 2-methoxyethanamine (0.017 mL, 0.2 mmol) was added and the solution was stirred at room temperature 2 days. The solution was concentrated and the residue was dissolved in ethyl acetate. The ethyl acetate layer was separated, extracted with water, and dried with brine. The crude product was purified on silica gel using 10-30% methanol/ethyl acetate as the eluent. The product fractions were concentrated to give a tan solid (14.2 mg, 32.2%).

$^1$H NMR (400 MHz, chloroform-d) δ ppm 3.12 (s, 1H) 3.35 (s, 3H) 3.52 (d, J=5.29 Hz, 2H) 3.56-3.67 (m, 2H) 4.11 (d, J=6.55 Hz, 1H) 6.25 (d, J=11.08 Hz, 1H) 7.32 (ddd, J=7.55, 4.78, 1.26 Hz, 1H) 7.42 (t, J=5.54 Hz, 1H) 7.49 (d, J=8.31 Hz, 1H) 7.53 (d, J=1.76 Hz, 1H) 7.71 (dd, J=8.31, 2.01 Hz, 1H) 7.74-7.82 (m, 2H) 8.09 (d, J=9.82 Hz, 1H) 8.52 (d, J=4.78 Hz, 1H).

LCMS (5-95% acetonitrile/water/10 mM ammonium acetate; 5 ml/min, 4 min gradient, Xbridge C18 4.6×50 mm 5 u, 254 nm) Rt=1.43 min, 100%, ES$^+$=386, 387.

HPLC (5-95% acetonitrile/water/10 mM ammonium acetate; 1 ml/min, 15 min gradient, Xterra C18 4.6×150 mm S3.5, 254 nm): Rt=8.18 min, 98.5%.

HPLC (5-95% acetonitrile/water/10 mM ammonium acetate; 1 ml/min, 15 min gradient, Xbridge C18 4.6×150 mm S3.5, 254 nm): Rt=7.97 min, 100%.

The invention claimed is:

1. The compound 8-Ethynyl-N-(2-methoxyethyl)-6-phenyl-4H-benzo[f]imidazo[1,5-a][1,4]diazepine-3-carboxamide, or a pharmaceutically acceptable salt thereof.

2. A composition comprising a pharmaceutically acceptable amount of a compound of claim 1 and a pharmaceutically acceptable carrier.

3. A method of treating a disorder comprising administering an effective amount of a compound of claim 1 to a patient wherein the disorder is selected from the group consisting of anxiety, seizures, convulsions, and cognitive disorders.

4. The method of claim 3 where the disorder is anxiety.

5. The method of claim 3 where the disorder is seizures or convulsions.

6. The method of claim 3 where the disorder is cognitive disorders.

* * * * *

UNITED STATES PATENT AND TRADEMARK OFFICE
CERTIFICATE OF CORRECTION

PATENT NO.        : 8,119,629 B2
APPLICATION NO.   : 12/240237
DATED             : February 21, 2012
INVENTOR(S)       : Ronald J. Mattson Page 1 of 1

It is certified that error appears in the above-identified patent and that said Letters Patent is hereby corrected as shown below:

On the Title Page:

Item (73), Assignee, change "Bristol-Meyers" to -- Bristol-Myers --.

Signed and Sealed this
Eighteenth Day of March, 2014

Michelle K. Lee
*Deputy Director of the United States Patent and Trademark Office*